US011981649B2

(12) United States Patent
Guenthner

(10) Patent No.: US 11,981,649 B2
(45) Date of Patent: *May 14, 2024

(54) COMPOSITION AND METHOD FOR MANUFACTURING RESINS

(71) Applicant: Cambium Biomaterials, Inc., Berkeley, CA (US)

(72) Inventor: Andrew Guenthner, Berkeley, CA (US)

(73) Assignee: CAMBIUM BIOMATERIALS, INC., Berkeley, CA (US)

( * ) Notice: Subject to any disclaimer, the term of this patent is extended or adjusted under 35 U.S.C. 154(b) by 680 days.

This patent is subject to a terminal disclaimer.

(21) Appl. No.: 17/089,635

(22) Filed: Nov. 4, 2020

(65) Prior Publication Data
US 2021/0130310 A1    May 6, 2021

Related U.S. Application Data

(60) Provisional application No. 62/931,116, filed on Nov. 5, 2019, provisional application No. 62/931,115, filed
(Continued)

(51) Int. Cl.
*C07D 303/23* (2006.01)
*C08G 59/02* (2006.01)
(Continued)

(52) U.S. Cl.
CPC ......... *C07D 303/23* (2013.01); *C08G 59/022* (2013.01); *C08G 59/28* (2013.01);
(Continued)

(58) Field of Classification Search
CPC .... C07D 303/23; C08G 59/022; C08G 59/28; C08G 59/32; C08G 59/3254; C08J 3/28;
(Continued)

(56) References Cited

U.S. PATENT DOCUMENTS

2011/0046266 A1   2/2011   Hefner, Jr. et al.
2014/0275343 A1   9/2014   Hefner, Jr. et al.
(Continued)

FOREIGN PATENT DOCUMENTS

WO   WO-2021092074 A1   5/2021

OTHER PUBLICATIONS

Iamsaard et al. "Fluorinated Azobenzenes for Shape-Persistent Liquid Crystal Polymer Networks" Supplemental information. Angewandte Chemie. 2016, 55 (Year: 2016).*
(Continued)

*Primary Examiner* — Andrew J. Oyer
(74) *Attorney, Agent, or Firm* — Burris Law, PLLC

(57) ABSTRACT

Certain embodiments of the invention described herein comprise a composition of matter, and method for preparing the same, which provide the benefits of pre-reaction molecular configuration favoring high liquidity properties, and post-reaction configuration that favors mechanical strength, stiffness, and properties associated with high viscous and/or solid-state materials. In some embodiments, the composition of matter can comprise relaxing photo-isomerizable fragments, of which a fraction can be transformed from trans to cis configurations upon exposure to a photon source. In some embodiments, the composition of matter further comprises thermally reactive fragments, of which can enable thermal solidification of a mixture upon exposure to elevated temperatures. In some embodiments, a composition of matter can be combined with reinforcing additives to form a prepreg combination.

1 Claim, 3 Drawing Sheets

Related U.S. Application Data on Nov. 5, 2019, provisional application No. 62/931,118, filed on Nov. 5, 2019.

(51) Int. Cl.
| | |
|---|---|
| *C08G 59/28* | (2006.01) |
| *C08G 59/32* | (2006.01) |
| *C08J 3/28* | (2006.01) |
| *C08J 5/02* | (2006.01) |
| *C08J 5/24* | (2006.01) |
| *C08K 5/1515* | (2006.01) |
| *C08K 5/23* | (2006.01) |
| *C08L 57/00* | (2006.01) |
| *C08L 63/00* | (2006.01) |
| *C08L 87/00* | (2006.01) |

(52) U.S. Cl.
CPC ............ *C08G 59/32* (2013.01); *C08J 3/28* (2013.01); *C08J 5/02* (2013.01); *C08J 5/24* (2013.01); *C08K 5/1515* (2013.01); *C08K 5/23* (2013.01); *C08L 57/00* (2013.01); *C08L 63/00* (2013.01); *C08L 87/00* (2013.01); *C08J 2300/24* (2013.01)

(58) Field of Classification Search
CPC ....... C08J 5/24; C08J 2300/24; C08K 5/1515; C08K 5/23; C08L 57/00; C08L 63/00; C08L 87/00; C08F 212/32
See application file for complete search history.

(56) References Cited

U.S. PATENT DOCUMENTS

| | | | | |
|---|---|---|---|---|
| 2016/0032043 | A1* | 2/2016 | von Recum | C07C 235/34 523/400 |
| 2017/0240811 | A1* | 8/2017 | Li | C09K 19/3814 |
| 2019/0256644 | A1 | 8/2019 | Hefner et al. | |
| 2021/0130534 | A1 | 5/2021 | Guenthner | |
| 2021/0130579 | A1 | 5/2021 | Guenthner | |

OTHER PUBLICATIONS

PCT/US2020/058959 International Preliminary Report on Patentability dated May 10, 2022.
Agolini et al., Synthesis and Properties of Azoaromatic Polymers. Macromolecules 3(3): 349-351 (1970).
Bis[4-(oxiran-2-ylmethyl)phenyl]diazene. PubChem CID 59790653 (2012).
Bleger et al., o-Fluoroazobenzenes as Readily Synthesized Photoswitches Offering Nearly Quantitative Two-Way Isomerization with Visible Light. J. Am. Chem. Soc. 134(51): 20597-20600 (2012).
Cambrea et al., Processable cyanate ester resin from Cis resveratrol. Polymer Chemistry 55: 971-980 (2017).
Garrison et al., Synthesis and Characterization of High-Performance, Bio-Based Epoxy-Amine Networks Derived from Resveratrol. ACS Sustainable Chem. Eng. 8(37): 14137-14149 (2020).
Guenthner et al., Mechanisms of Decreased Moisture Uptake in Ortho-Methylated Di(cyanate ester) Networks. Macromolecules 47(22): 7691-7700 (2014).
Hubbard et al., Curing of a Bisphenol E Based Cyanate Ester Using Magnetic Nanoparticles as an Internal Heat Source through Induction Heating. ACS Appl. Mater. Interfaces 5(21): 11329-11335 (2013).
Moore et al., Molecular modeling of polycyanurates to predict thermophysical properties. American Chemical Society Fall 2019 National Meeting and Expo, San Diego, CA. Aug. 25-29, 2019.
Mutasher et al., Small-Scale Filament Winding Machine for Producing Fiber Composite Products. Journal of Engineering Science and Technology 7(2): 156-158 (2012).
PCT/US2020/058959 International Search Report and Written Opinion dated Mar. 18, 2021.
Reams et al., Effect of Chemical Structure and Network Formation on Physical Properties of Di(Cyanate Ester) Thermosets. ACS Appl. Mater. Interfaces 4(2): 527-535 (2012).
Yang et al., Highly Efficient Synthesis of Phenols by Copper-Catalyzed Hydroxylation of Aryl Iodides, Bromides, and Chlorides. Org. Lett 13(16): 4340-4343 (2011).

* cited by examiner

COMPOSITION AND METHOD FOR MANUFACTURING RESINS

CROSS-REFERENCE

This application claims priority to U.S. Provisional Application No. 62/931,115, filed Nov. 5, 2019, U.S. Provisional Application No. 62/931,116, filed Nov. 5, 2019, and U.S. Provisional Application No. 62/931,118, filed Nov. 5, 2019, all of which are incorporated by reference herein in their entirety.

BACKGROUND

Polymer and composite materials can provide tailored characteristics that benefit specific applications of use. Examples of such characteristics include low gravimetric density, resistance to dissolution by fluids, resistance to corrosion, and mechanical strength and toughness. These characteristics derive from their composition of matter. Naturally, materials having different compositions of matter can exhibit different types of characteristics. For example, compositions of matter featuring molecules with atoms strongly bonded to one another in a prolate configuration offer strength, stiffness, and resistance to dissolution, but compositions of matter featuring molecules in these geometric configurations also feature a low level of fluidity, manifested as either a crystalline phase with a high melting point and a high fluid viscosity. However, in some cases, materials may exhibit different characteristics due to the differences in the respective molecular geometry, for example, having isomers of some of the respective molecules.

SUMMARY

Composites and polymers, including thermosets and/or cured resins, are often limited to their respective genus of properties as exhibited, and thereby difficult to satisfy requirements for diverse properties. For example, materials with a low viscosity, thereby increased liquidity, are unable to provide much of the benefits exhibited by solid-state composites. Such solid-state benefits can include strength, control of shrinkage, resistance to oxidation, etc. Similarly, materials having solid-state benefits are unable to provide much of benefits exhibited by low viscous composites, such as ease of mixing with other ingredients, ability to flow/transport, and ability to speed up reactions rates at lower temperatures. Determining compositions that can satisfy multiple performance requirements is difficult, and time-consuming, due to the general inability of readily available single compositions of matter than can simultaneously satisfy many diverse requirements. For example, typically, the "liquidity" exhibited in materials are due to a permanent mixture of "cis" and "trans" configurations, with a predominance of "cis" configurations. Conversely, the solid-state benefits exhibited in materials are due to a permanent mixture of cis and trans configurations, with a predominance of trans configurations. As such, the permanence of these configurations provide difficulties in preparing materials wherein the composition provides physical properties, such as liquidity and viscosity, that is predominantly fixed.

Provided in some embodiments herein is a composition of matter, and method for preparing the same, which provide the benefits of pre-reaction molecular configuration favoring high liquidity properties, and post-reaction configuration that favors mechanical strength, stiffness, and properties associated with high viscous and/or solid-state materials. In some embodiments, the composition of matter can comprise relaxing photo-isomerizable fragments (or "radicals"), of which a fraction can be transformed from trans to cis configurations upon exposure to a photon source. In some embodiments, the composition of matter further comprises thermally reactive fragments, of which can enable thermal solidification of a mixture upon exposure to elevated temperatures. In some embodiments, a composition of matter can be combined with reinforcing additives to form a prepreg combination. In some embodiments, additive packages and formulated resin products comprise the compositions of matter.

In some embodiments, provided herein is a composition comprising a plurality of molecules, the plurality of molecules collectively comprising: a) a plurality of photo-isomerizable radicals; b) a plurality of thermally reactive radicals; and c) a plurality of thermally stable radicals, wherein each photo-isomerizable radical optionally comprises at least one thermally stable radical(s). In some embodiments, discrete radicals are connected 1) directly, or 2) through a linker such as a substituted or unsubstituted alkyl or heteroalkyl.

In certain embodiments provided herein, radicals provided herein are present in one or more component parts. For example, in some embodiments, a first component comprises at least one of the recited radicals and a second component comprises at least a second one of the recited radicals. For example, where photo-isomerizable radicals are represented by A, thermally reactive radicals are represented by B, and thermally stable radicals are represented by C, a first component optionally comprises A; B; A and one or more B; A, one or more B, and one or more C; A and one or more C; or one or more B and one or more C. Within the first component, however, the molecules are optionally the same or different. In such an example, a second component optionally comprises a radical or collection of radicals selected from the same list, but that is a different collection than the first component.

In some embodiments, provided herein is a composition comprising a first component, wherein the first component comprises a plurality of first component molecules, the plurality of first component molecules each comprising a) a photo-isomerizable radical; b) at least one thermally reactive radical; and c) at least one thermally stable radical(s), wherein the photo-isomerizable radical optionally comprises the at least one thermally stable radical(s). In some embodiments, the composition further comprising a second component comprising a plurality of second component molecules, the plurality of second component molecules each comprising at least one thermally reactive radical and at least one thermally stable radical.

In some embodiments, provided herein is a composition comprising a first component and a second component, wherein the first component comprises a plurality of first component molecules, the plurality of first component molecules each comprising a photo-isomerizable radical, and the second component comprises a plurality of second component molecules, the plurality of second component molecules each comprising a) at least one thermally reactive radical, and b) at least one thermally stable radical.

In some embodiments, provided herein is a composition comprising a first component and a second component, wherein the first component comprises a plurality of first component molecules, the plurality of first component molecules each comprising a photo-isomerizable radical that comprises at least one thermally stable radical, and the second component comprises a plurality of second component molecules, the plurality of second component molecules each comprising at least one thermally reactive radical.

In some embodiments, such as in any composition described herein, the photo-isomerizable radical comprises the at least one thermally stable radical. In some embodiments, such as in any composition described herein, the ratio of number of thermally reactive radicals to total number of molecules (e.g., in the composition, absent solvent) is at least 1:1. In some embodiments, such as in any composition described herein, the ratio of number of thermally reactive radicals to total number of molecules (e.g., in the composition, absent solvent) is at least 2:1. In some embodiments, such as in any composition described herein, the ratio of number of thermally reactive radicals to total number of molecules (e.g., in the composition, absent solvent) is greater than 2:1.

In some embodiments, such as in any composition described herein, the ratio of number of photo-isomerizable radical(s) to thermally reactive radical(s) is about 1:1000 to about 10:1. In some embodiments, such as in any composition described herein, the ratio of number of thermally stable radicals to total number of molecules (e.g., absent solvent) is about 1:2 to about 10:1.

In some embodiments, such as in any composition described herein, the composition is a resin. In some instances, such as in any composition described herein, the composition is a resin additive. In some embodiments, such as in any composition described herein, each photo-isomerizable radical independently has a molecular weight of about 165 g/mol to about 1075 g/mol. In some embodiments, such as in any composition described herein, each thermally reactive radical independently has a molecular weight of about 50 g/mol to about 500 g/mol.

In some embodiments, such as in any composition described herein, each photo-isomerizable radical comprise a structure >X=Y<, wherein each X is independently a carbon atom (C) or a nitrogen atom (N), and each Y is independently C or N. In some embodiments, such as in any composition described herein, the photo-isomerizable radical is an azo-benzene, a stilbene, an aromatic cyanoethene, a hemithioindigo, a pyrroline, or an isoindolinone.

In some embodiments, such as in any composition described herein, each thermally stable radical independently is or comprises a substituted or unsubstituted aryl or substituted or unsubstituted heteroaryl. In some embodiments, such as in any composition described herein, each thermally stable radical is independently selected from a substituted or unsubstituted ring, the ring being benzene, naphthalene, anthracene, phenanthrene, pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, xanthene, benzofuran, isobenzofuran, dibenzofuran, benzothiophene, dibenzothiophene, benzoxazole, benzisoxazole, phenoxazine, benzothiazole, benzisothiazole, phenothiazine, azulene, or an aforementioned ring in which one or more non-adjacent nitrogen or oxygen atoms in a ring is substituted by a carbonyl having a carbon as part of the ring.

In some embodiments, such as in any composition described herein, each thermally reactive radical is independently selected from hydroxyl, thiol, amine, epoxide, cyanate ester, phthalonitrile, acetylene, maleimide, melamine, benzoxazine, amic acid, phenyl ethynyl, silanol, a silazane, a phosphoric acid salt, phosphoric acid ester, or phosphoric acid anhydride.

In some embodiments, such as in any composition described herein, the molecules of the first component or photo-isomerizable radical, independently, comprises of a structure of Formula I:

Formula I

In some embodiments, referring to Formula I, wherein X and Y are independently C or N; $R^1$ and $R^2$ are independently H (Hydrogen atom), halo, cyano, substituted aryl, unsubstituted aryl, substituted heteroaryl, or unsubstituted heteroaryl; or $R^1$ and $R^2$ are taken together to form a substituted or unsubstituted ring; and $R^3$ and $R^4$ are independently H, halo, cyano, substituted aryl, unsubstituted aryl, substituted heteroaryl, or unsubstituted heteroaryl; and wherein at least one of $R^1$ and $R^2$ is not H, at least one of $R^3$ and $R^4$ is not H, and $R^1$, $R^2$, $R^3$, and $R^4$ are not all the same.

In some embodiments, such as in any composition described herein, wherein in one or more of the molecules or photo-isomerizable radicals, at least one or both of X and Y is N. In some embodiments, such as in any composition described herein, at least one or both of X and Y is N.

In some embodiments, such as in any composition described herein, all or a fraction of the first component molecules have a structure of Formula I, wherein $R^1$ has a structure of $Ar^1$-$L^{1a}$-$Ar^{1a}$—$R^{1a}$; wherein $Ar^1$ is substituted aryl, unsubstituted aryl, substituted heteroaryl, or unsubstituted heteroaryl; $L^{1a}$ is a bond, —O—, amine, —S—, or carboxyl; $Ar^{1a}$ is substituted aryl, unsubstituted aryl, substituted heteroaryl, or unsubstituted heteroaryl; and $R^{1a}$ is H, a thermally reactive radical, or a linker-thermally reactive radical (e.g., wherein the linker is a —O—, —S—, alkyl, heteroalkyl).

In some embodiments, such as in any composition described herein, all or a fraction of the first component molecules have a structure of Formula I, wherein $R^2$ has a structure of $Ar^2$-$L^{2a}$-$Ar^{2a}$—$R^{2a}$; wherein $Ar^2$ is substituted aryl, unsubstituted aryl, substituted heteroaryl, or unsubstituted heteroaryl; $L^{2a}$ is a bond, —O—, amine, —S—, or carboxyl; $Ar^{2a}$ is substituted aryl, unsubstituted aryl, substituted heteroaryl, or unsubstituted heteroaryl; and $R^{2a}$ is H, a thermally reactive radical, or a linker-thermally reactive radical (e.g., wherein the linker is a —O—, —S—, alkyl, heteroalkyl).

In some embodiments, such as in any composition described herein, all or a fraction of the first component molecules have a structure of Formula I, wherein $R^3$ has a structure of $Ar^3$-$L^{3a}$-$Ar^{3a}$—$R^{3a}$; wherein $Ar^3$ is substituted aryl, unsubstituted aryl, substituted heteroaryl, or unsubstituted heteroaryl; $L^{3a}$ is a bond, —O—, amine, —S—, or carboxyl; $Ar^{3a}$ is substituted aryl, unsubstituted aryl, substituted heteroaryl, or unsubstituted heteroaryl; and $R^{3a}$ is H, a thermally reactive radical, or a linker-thermally reactive radical (e.g., wherein the linker is a —O—, —S—, alkyl, heteroalkyl).

In some embodiments, such as in any composition described herein, all or a fraction of the first component molecules have a structure of Formula I, wherein $R^4$ has a structure of Ar⁴-L⁴ᵃ-Ar⁴ᵃ—R⁴ᵃ; wherein Ar⁴ is substituted aryl, unsubstituted aryl, substituted heteroaryl, or unsubstituted heteroaryl; L⁴ᵃ is a bond, —O—, amine, —S—, or carboxyl; Ar⁴ᵃ is substituted aryl, unsubstituted aryl, substituted heteroaryl, or unsubstituted heteroaryl; and R⁴ᵃ is H, a thermally reactive radical, or a linker-thermally reactive radical (e.g., wherein the linker is a —O—, —S—, alkyl, heteroalkyl).

In some embodiments, such as in any composition described herein, all or a fraction of the molecules of the first component or photo-isomerizable radical, independently have a structure of Formula II:

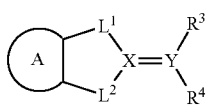

Formula II

In some embodiments, referring to Formula II, wherein X is C; Y is C or N; $L^1$ and $L^2$ are independently a bond, sulfur, oxygen, amino, amide (lactam), alkylenyl, or carboxyl, wherein the ring comprising $L^1$ and $L^2$ is a 5 or 6 membered ring; and $R^3$ and $R^4$ are independently H, halo, cyano, substituted aryl or unsubstituted aryl, or substituted heteroaryl or unsubstituted heteroaryl; A is substituted aryl or unsubstituted aryl or substituted heteroaryl or unsubstituted heteroaryl; and wherein at least one of $R^3$ and $R^4$ is not H, and $R^3$ and $R^4$ are not all the same.

In some embodiments, such as in any composition described herein, wherein all or a fraction of the molecules of the first component, independently have a structure of Formula III (e.g., trans configuration):

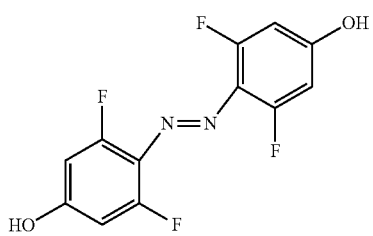

Formula III

In some embodiments, such as in any composition described herein, wherein all or a fraction of the molecules of the first component, independently have a structure of Formula IV (e.g., cis configuration):

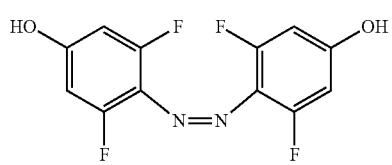

Formula IV

In some embodiments, such as in any composition described herein, one or more photo-isomerizable radicals of the photo-isomerizable radicals is an azo-benzene or a stilbene, or comprises a structure of Formula III or Formula IV. In some embodiments, such as in any composition described herein, one or more thermally reactive radicals of the thermally reactive radicals is an epoxide. In some embodiments, such as in any composition described herein, one or more thermally stable radicals of the thermally stable radicals is selected from a substituted or unsubstituted benzene of an azo-benzene or a stilbene. In some embodiments, such as in any composition described herein, a) one or more photo-isomerizable radicals of the photo-isomerizable radicals is an azo-benzene, or a stilbene, or comprises a structure of Formula III or Formula IV; b) one or more thermally reactive radicals of the thermally reactive radicals is an epoxide; and c) one or more thermally stable radicals of the thermally stable radicals is selected from a substituted or unsubstituted benzene of an azo-benzene or a stilbene.

In some embodiments, disclosed herein is a composition comprising a compound having a structure of Formula V (shown in cis configuration as an example):

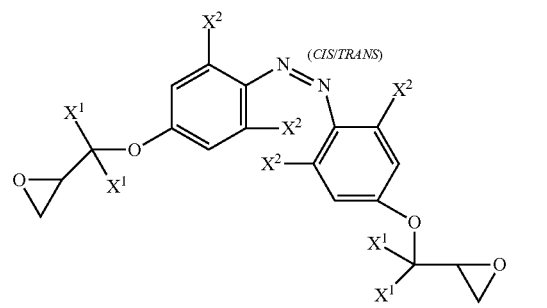

Formula V

In some embodiments, a) each $X^1$ is independently CH₃ or H; b) each $X^2$ is independently selected from the group consisting of: H, F, a halomethyl (e.g., a fluoromethyl such as CF₃), and CH₃; and c) the Formula V structure has a cis or trans configuration (as indicated in the shown Formula V). In some embodiments, each $X^1$ is H and each $X^2$ is F.

In some embodiments, disclosed herein is a composition comprising a compound having a structure herein, such as of Formula V, in a cis-to-trans mol ratio (e.g., around the center N═N or C═C moiety) of about 0:100 to about 100:0, such as about 1:99 to about 99:1, about 10:90 to about 90:10, about 5:95 to about 25:75, about 30:70 to about 70:30, or about 50:50. In some embodiments, disclosed herein is a composition comprising a compound having a structure herein, such as of Formula V, in a cis-to-trans mol ratio (e.g., around the center N═N or C═C moiety) of about 1:99 to about 100:0, such as about 10:90 to about 100:0, about 20:80 to about 100:0, about 30:70 to about 100:00, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, disclosed herein is a composition comprising a compound having a structure of Formula VI (shown in cis configuration as an example):

Formula VI

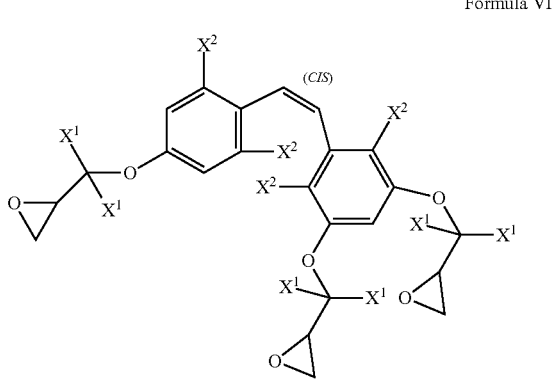

In some embodiments, a) each $X^1$ is independently $CH_3$ or H, b) each $X^2$ is independently selected from the group consisting of: H, F, a halomethyl (e.g., fluoromethyl such as $CF_3$), and $CH_3$, and c) the Formula VI structure has a cis configuration (as indicated in the shown Formula VI). In some embodiments, each $X^1$ and $X^2$ are H.

In some embodiments, disclosed herein is a composition comprising a compound having a structure herein, such as of Formula VI, in a cis-to-trans mol ratio (e.g., around the center C=C or N=N moiety) of about 0:100 to about 100:0, such as about 1:99 to about 99:1, about 10:90 to about 90:10, about 5:95 to about 25:75, about 30:70 to about 70:30, or about 50:50. In some embodiments, disclosed herein is a composition comprising a compound having a structure herein, such as of Formula VI, in a cis-to-trans mol ratio (e.g., around the center C=C or N=N moiety) of about 1:99 to about 100:0, such as about 10:90 to about 100:0, about 20:80 to about 100:0, about 30:70 to about 100:00, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, such as in any composition described herein, wherein the composition further comprises a reagent. In some embodiment, the reagent is selected from the group consisting of formaldehyde, acid chloride, alkyl chloride, alkyl bromide, alkyl iodide, metal hydroxide, aromatic cyanate ester, aromatic phthalonitrile, aryl amine, alkyl amine, or any combination of two or more thereof. In some embodiments, the reagent comprises one or more dianiline compounds. In some embodiments, the one or more dianiline compounds are independently selected from the group consisting of: bis(4-aminophenyl)methane, bis(3-ethyl, 5-methy, 4-aminophenyl)methane, bis(3,3-diethyl, 4-aminophenyl)methane, meta-phenylenediamine, para-phenylenediamine, ortho-phenylenediamine, 4,4'-oxy-dianiline, 3,4'-oxy-dianiline, 3,3'-diaminodiphenylsulfone, 4,4'diaminodiphenulsulfone, 4,4'-Bis(3-aminophenoxy)diphenyl sulfone 4,4'-diaminodiphenylsulfide, 4,4'-(1,3-phenylenedioxy)dianiline, 4,4'-(9-fluorenylidene)dianiline, 4,4'-(hexafluoroisopropylidene)dianiline, 3,3'-(hexafluoroisopropylidene)dianiline, 4,4'-(1,1'-biphenyl-4,4'-diyldioxy) dianiline, 4,4'-(4,4'-isopropylidenediphenyl-1,1'-diyldioxy) dianiline, 4,4'-(Hexafluoroisopropylidene)bis(p-phenyleneoxy)dianiline, and any combination thereof.

In some embodiments, such as in any composition described herein, wherein the composition further comprises at least one additional component (for e.g., a third component). In some embodiments, each of the at least one additional component comprises at least one thermally stable radical and at least one thermally reactive radical. In some embodiments, the at least one additional component comprises Aromatic cyanate ester resin, including Bispheol A dicyanate, Bisphenol E dicyanate, Bisphenol M dicyanate, novolac-based dicyanate (PT resin, PT-15, PT-30), Bisphenol S dicyanate, 4,4'-dicyanato-diphenyl ether, resveratrol tricyanate, aromatic phthalonitrile resins including Bisphenol A phthalonitrile, oligo(ether) phthaonitrile resins, resveratrol phthalonitrile, oligomers thereof, incompletely converted versions thereof based on the parent phenols, or any combination thereof.

In some embodiments, such as in any composition described herein, two or more discrete radicals are connected i) directly, or ii) through a linker, such as a substituted or unsubstituted alkyl or heteroalkyl.

In some embodiments, provided herein is a kit comprising a composition, such as in any composition described herein, and one or more packages. In some embodiments, the one or more package contains any composition described herein. In some embodiments, separate components of the composition are contained within separate compartments of the one or more packages.

In some embodiments, provided herein is a method for manufacturing a composition, wherein the method comprises a) providing a plurality of molecules, the plurality of molecules collectively comprising a plurality of photo-isomerizable radicals, a plurality of thermally reactive radicals, and a plurality of thermally stable radicals, wherein the photo-isomerizable radicals optionally comprises some or all of the thermally stable radicals; b) combining the plurality of molecules to form a combination; and c) mixing the combination with an optional solvent. In some embodiments, said method further comprises exposing the combination to a photon source.

In some embodiments, such as in any method described herein, the plurality of photo-isomerizable radical comprise one or more type of photo-isomerizable radical, the plurality of thermally reactive radicals comprise one or more type of thermally reactive radical, and the thermally stable radicals comprise one or more type of thermally stable radical.

In some embodiments, such as in any method described herein, wherein the plurality of molecules comprise a first component, wherein the first component comprises a plurality of first component molecules, the plurality of first component molecules each comprising a photo-isomerizable radical. In some embodiments, each of the first component molecules further comprise a) at least one thermally reactive radical; and b) at least one thermally stable radical(s), wherein the photo-isomerizable radical optionally comprises the at least one thermally stable radical(s). In some embodiments, such as in any method described herein, the plurality of molecules comprises a second component comprising a plurality of second component molecules, the plurality of second component molecules each comprising at least one thermally reactive radical and at least one thermally stable radical.

In some embodiments, such as in any method described herein, discrete radicals are connected i) directly, or ii) through a linker, such as a substituted or unsubstituted alkyl or heteroalkyl.

In some embodiments, such as in any method described herein, the ratio of number of thermally reactive radicals to total number of molecules (e.g., in the combination, absent solvent) is at least 1:1. In some embodiments, such as in any method described herein, the ratio of number of thermally reactive radical to total number of molecules (e.g., in the combination, absent solvent) is at least 2:1. In some embodiments, such as in any method described herein, the ratio of number of thermally reactive radicals to total number of molecules is greater than 2:1 (e.g., in the combination, absent solvent).

In some embodiments, such as in any method described herein, the ratio of number of photo-isomerizable radical(s) to thermally reactive radical(s) is about 1:1000 to about 10:1. In some embodiments, such as in any method described herein, the ratio of number of thermally stable radical(s) to total number of molecules (e.g., absent solvent) is about 1:2 to about 10:1.

In some embodiments, such as in any method described herein, each photo-isomerizable radical independently has a molecular weight of about 165 g/mol to about 1075 g/mol. In some embodiments, such as in any method described herein, each thermally reactive radical independently has a molecular weight of about 50 g/mol to about 500 g/mol.

In some embodiments, such as in any method described herein, each photo-isomerizable radical comprise a structure >X=Y<, wherein each X is independently a carbon atom (C) or a nitrogen atom (N), and each Y is independently C or N. In some embodiments, such as in any method described herein, the photo-isomerizable radical is an azo-benzene, a stilbene, an aromatic cyanoethene, a hemithioindigo, a pyrroline, or an isoindolinone.

In some embodiments, such as in any method described herein, each thermally stable radical independently is or comprises a substituted or unsubstituted aryl or substituted or unsubstituted heteroaryl. In some embodiments, such as in any method described herein, each thermally stable radical is independently selected from a substituted or unsubstituted ring, the ring being benzene, naphthalene, anthracene, phenanthrene, pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, xanthene, benzofuran, isobenzofuran, dibenzofuran, benzothiophene, dibenzothiophene, benzoxazole, benzisoxazole, phenoxazine, benzothiazole, benzisothiazole, phenothiazine, azulene, or an aforementioned ring in which one or more non-adjacent nitrogen or oxygen atoms in a ring is substituted by a carbonyl having a carbon as part of the ring.

In some embodiments, such as in any method described herein, each thermally reactive radical is independently selected from hydroxyl, thiol, amine, epoxide, cyanate ester, phthalonitrile, acetylene, maleimide, melamine, benzoxazine, amic acid, phenyl ethynyl, silanol, a silazane, a phosphoric acid salt, phosphoric acid ester, or phosphoric acid anhydride.

In some embodiments, such as in any method described herein, the molecules of the first component or photo-isomerizable radical, independently, comprises of a structure of Formula I:

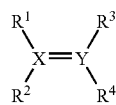

Formula I

In some embodiments, referring to Formula I, wherein X and Y are independently C or N; $R^1$ and $R^2$ are independently H (Hydrogen atom), halo, cyano, substituted aryl, unsubstituted aryl, substituted heteroaryl, or unsubstituted heteroaryl; or $R^1$ and $R^2$ are taken together to form a substituted or unsubstituted ring; and $R^3$ and $R^4$ are independently H, halo, cyano, substituted aryl, unsubstituted aryl, substituted heteroaryl, or unsubstituted heteroaryl; and wherein at least one of $R^1$ and $R^2$ is not H, at least one of $R^3$ and $R^4$ is not H, and $R^1$, $R^2$, $R^3$, and $R^4$ are not all the same.

In some embodiments, such as in any method described herein, in one or more of the molecules or photo-isomerizable radicals, at least one or both of X and Y is N. In some embodiments, such as in any method described herein, at least one or both of X and Y is N.

In some embodiments, such as in any method described herein, all or a fraction of the first component molecules have a structure of Formula I, wherein $R^1$ has a structure of $Ar^1$-$L^{1a}$-$Ar^{1a}$—$R^{1a}$; wherein $Ar^1$ is substituted aryl, unsubstituted aryl, substituted heteroaryl, or unsubstituted heteroaryl; $L^{1a}$ is a bond, —O—, amine, —S—, or carboxyl; Ar1a is substituted aryl, unsubstituted aryl, substituted heteroaryl, or unsubstituted heteroaryl; and $R^{1a}$ is H, a thermally reactive radical, or a linker-thermally reactive radical (e.g., wherein the linker is a —O—, —S—, alkyl, heteroalkyl).

In some embodiments, such as in any method described herein, all or a fraction of the first component molecules have a structure of Formula I, wherein $R^2$ has a structure of $Ar^2$-$L^{2a}$-$Ar^{2a}$—$R^{2a}$; wherein $Ar^2$ is substituted aryl, unsubstituted aryl, substituted heteroaryl, or unsubstituted heteroaryl; $L^{2a}$ is a bond, oxygen (—O—), amine, sulfur (—S—), or carboxyl; $Ar^{2a}$ is substituted aryl, unsubstituted aryl, substituted heteroaryl, or unsubstituted heteroaryl; and $R^{2a}$ is H, a thermally reactive radical, or a linker-thermally reactive radical (e.g., wherein the linker is a —O—, —S—, alkyl, heteroalkyl).

In some embodiments, such as in any method described herein, all or a fraction of the first component molecules have a structure of Formula I, wherein $R^3$ has a structure of $Ar^3$-$L^{3a}$-$Ar^{3a}$—$R^{3a}$; wherein $Ar^3$ is substituted aryl, unsubstituted aryl, substituted heteroaryl, or unsubstituted heteroaryl; $L^{3a}$ is a bond, —O—, amine, —S—, or carboxyl; $Ar^{3a}$ is substituted aryl, unsubstituted aryl, substituted heteroaryl, or unsubstituted heteroaryl; and $R^{3a}$ is H, a thermally reactive radical, or a linker-thermally reactive radical (e.g., wherein the linker is a —O—, —S—, alkyl, heteroalkyl).

In some embodiments, such as in any method described herein, all or a fraction of the first component molecules have a structure of Formula I, wherein $R^4$ has a structure of $Ar^4$-$L^{4a}$-$Ar^{4a}$—$R^{4a}$; wherein $Ar^4$ is substituted aryl, unsubstituted aryl, substituted heteroaryl, or unsubstituted heteroaryl; $L^{4a}$ is a bond, —O—, amine, —S—, or carboxyl; $Ar^{4a}$ is substituted aryl, unsubstituted aryl, substituted heteroaryl, or unsubstituted heteroaryl; and $R^{4a}$ is H, a thermally reactive radical, or a linker-thermally reactive radical (e.g., wherein the linker is a —O—, —S—, alkyl, heteroalkyl).

In some embodiments, such as in any method described herein, wherein all or a fraction of the molecules of the first component or photo-isomerizable radical, independently have a structure of Formula II:

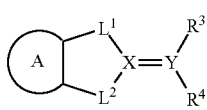

Formula II

In some embodiments, referring to Formula II, wherein X is C; Y is C or N; $L^1$ and $L^2$ are independently a bond, —S—, —O—, amino, amide (lactam), alkylenyl, or carboxyl, wherein the ring comprising $L^1$ and $L^2$ is a 5 or 6 membered ring; and $R^3$ and $R^4$ are independently H, halo, cyano, substituted aryl or unsubstituted aryl, or substituted heteroaryl or unsubstituted heteroaryl; A is substituted aryl or unsubstituted aryl, or substituted heteroaryl or unsubstituted heteroaryl; and wherein at least one of $R^3$ and $R^4$ is not H; $R^3$, and $R^4$ are not all the same.

In some embodiments, such as in any method described herein, wherein all or a fraction of the molecules of the first component, independently have a structure of Formula III (e.g., trans configuration):

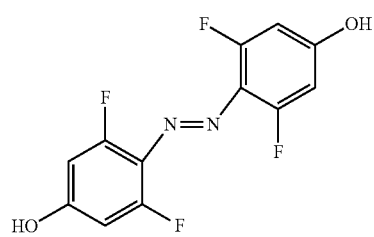

Formula III

In some embodiments, such as in any method described herein, wherein all or a fraction of the molecules of the first component, independently have a structure of Formula IV (for e.g., cis configuration):

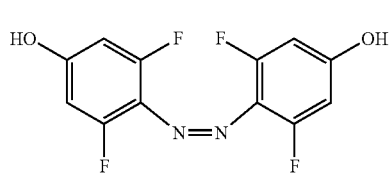

Formula IV

In some embodiments, such as in any method described herein, one or more photo-isomerizable radicals of the photo-isomerizable radicals is an azo-benzene or a stilbene, or comprises a structure of Formula III or Formula IV. In some embodiments, such as in any method described herein, one or more thermally reactive radicals of the thermally reactive radicals is an epoxide. In some embodiments, such as in any method described herein, one or more thermally stable radicals of the thermally stable radicals is selected from a substituted or unsubstituted benzene of an azo-benzene or a stilbene. In some embodiments, such as in any method described herein, a) one or more photo-isomerizable radicals of the photo-isomerizable radicals is an azo-benzene, or a stilbene, or comprises a structure of Formula III or Formula IV; b) one or more thermally reactive radicals of the thermally reactive radicals is an epoxide; and c) one or more thermally stable radicals of the thermally stable radicals is selected from a substituted or unsubstituted benzene of an azo-benzene or a stilbene.

In some embodiments, such as in any method described herein, the composition comprises a compound having a structure of Formula V (shown in cis configuration as an example):

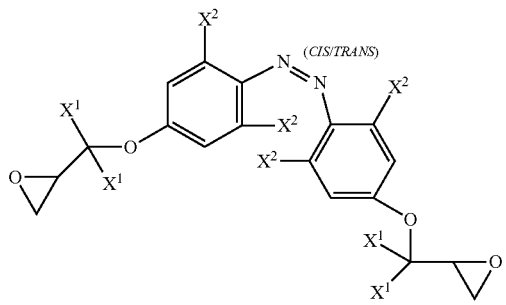

Formula V

In some embodiments, a) each $X^1$ is independently $CH_3$ or H; b) each $X^2$ is independently selected from the group consisting of: H, F, a halomethyl (e.g., a fluoromethyl such as $CF_3$), and CH3; and c) the Formula V structure has a cis or trans configuration (as indicated in the shown Formula V). In some embodiments, each $X^1$ is H and each $X^2$ is F.

In some embodiments, such as in any method described herein, the composition comprises a compound having a structure herein, such as of Formula V, in a cis-to-trans mol ratio (e.g., around the center N=N or C=C moiety) of about 0:100 to about 100:0, such as about 1:99 to about 99:1, about 10:90 to about 90:10, about 5:95 to about 25:75, about 30:70 to about 70:30, or about 50:50. In some embodiments, such as in any method described herein, the composition comprises a compound having a structure herein, such as of Formula V, in a cis-to-trans mol ratio (e.g., around the center N=N or C=C moiety) of about 1:99 to about 100:0, such as about 10:90 to about 100:0, about 20:80 to about 100:0, about 30:70 to about 100:0, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, such as in any method described herein, the composition comprises a compound having a structure of Formula VI (shown in cis configuration as an example):

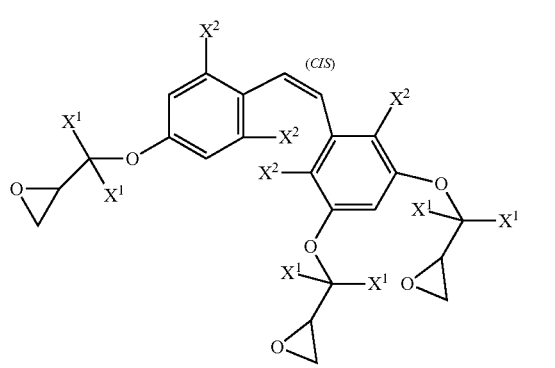

Formula VI

In some embodiments, a) each $X^1$ is independently $CH_3$ or H, b) each $X^2$ is independently selected from the group consisting of H, F, a halomethyl (e.g., fluoromethyl such as CF$_3$), and CH$_3$, and c) the Formula VI structure has a cis configuration (as indicated in the shown Formula VI). In some embodiments, each X$^1$ and X$^2$ are H.

In some embodiments, such as in any method described herein, the composition comprises a compound having a structure herein, such as of Formula VI, in a cis-to-trans mol ratio (e.g., around the center C=C or N=N moiety) of about 0:100 to about 100:0, such as about 1:99 to about 99:1, about 10:90 to about 90:10, about 5:95 to about 25:75, about 30:70 to about 70:30, or about 50:50. In some embodiments, such as in any method described herein, the composition comprises a compound having a structure herein, such as of Formula VI, in a cis-to-trans mol ratio (e.g., around the center C=C or N=N moiety) of about 1:99 to about 100:0, such as about 10:90 to about 100:0, about 20:80 to about 100:0, about 30:70 to about 100:00, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, such as in any method described herein, wherein the composition further comprises a reagent. In some embodiment, said reagent is selected from the group consisting of formaldehyde, acid chloride, alkyl chloride, alkyl bromide, alkyl iodide, metal hydroxide, aromatic cyanate ester, aromatic phthalonitrile, aryl amine, alkyl amine, or any combination of two or more thereof. In some embodiments, the reagent comprises one or more dianiline compounds. In some embodiments, the one or more dianiline compounds are independently selected from the group consisting of: bis(4-aminophenyl)methane, bis(3-ethyl, 5-methy, 4-aminophenyl)methane, bis(3,3-diethyl, 4-aminophenyl)methane, meta-phenylenediamine, para-phenylenediamine, ortho-phenylenediamine, 4,4'-oxy-dianiline, 3,4'-oxy-dianiline, 3,3'-diaminodiphenylsulfone, 4,4'diaminodiphenulsulfone, 4,4'-Bis(3-aminophenoxy)diphenyl sulfone 4,4'-diaminodiphenylsulfide, 4,4'-(1,3-phenylenedioxy)dianiline, 4,4'-(9-fluorenylidene)dianiline, 4,4'-(hexafluoroisopropylidene)dianiline, 3,3'-(hexafluoroisopropylidene)dianiline, 4,4'-(1,1'-biphenyl-4,4'-diyldioxy)dianiline, 4,4'-(4,4'-isopropylidenediphenyl-1,1'-diyldioxy)dianiline, 4,4'-(Hexafluoroisopropylidene)bis(p-phenyleneoxy)dianiline, and any combination thereof.

In some embodiments, such as in any method described herein, wherein the molecules of the combination comprise a first component (e.g., comprising a photo-isomerizable radical and, optionally, a thermally reactive radical and a thermally stable radical) and at least one additional component, the at least one additional component comprising at least one thermally stable radical and at least one thermally reactive radical. In some embodiments, the at least one additional component comprises Aromatic cyanate ester resin, including Bispheol A dicyanate, Bisphenol E dicyanate, Bisphenol M dicyanate, novolac-based dicyanate (PT resin, PT-15, PT-30), Bisphenol S dicyanate, 4,4'-dicyanatodiphenyl ether, resveratrol tricyanate, aromatic phthalonitrile resins including Bisphenol A phthalonitrile, oligo(ether) phthaonitrile resins, resveratrol phthalonitrile, oligomers thereof, incompletely converted versions thereof based on the parent phenols, or any combination thereof.

In some embodiments, such as in any method described herein, the combination comprises photo-isomerizable radical in a concentration of about 0.1 mmol/cc to about 10 mmol/cc. In some embodiments, such as in any method described herein, the combination comprises thermally reactive radical in a concentration of about 0.1 mmol/cc to about 10 mmol/cc. In some embodiments, such as in any method described herein, the combination comprises thermally stable radicals in a concentration of ≤2 g/cc. In some embodiments, such as in any method described herein, combining the molecules comprises combining them together and with a solvent (or other diluent or medium). In some embodiments, such as in any method described herein, combining the molecules comprises combining them together and with a solvent (or other diluent or medium), wherein the solvent (or other diluent or medium) is present in the combination is a concentration of about 0.1 wt. % to about 99.9 wt. % (e.g., the molecules can make up between 0.1 wt. % and 100 wt. % of the combination). In some embodiments, such as in any method described herein, wherein exposing the combination to a photon source provides photo-isomerization of all or some (e.g., about 10% to about 90% isomerized from trans to cis, such as about 20% to about 80%, such as about 50% to about 80%, such as about 70%) of the photo-isomerizable radicals. In some embodiments, such as in any method described herein, wherein exposing the combination to a photon source comprises providing 0.01 J to 1,000 J to the combination. In some embodiments, such as in any method described herein, wherein exposing the combination to a photon source comprises exposing the combination to an intensity of about 0.001 W to about 1,000 W per square cm. In some embodiments, such as in any method described herein, wherein exposing the combination to a photon source comprises exposing the combination to a wavelength (e.g., photon) a wavelength of about 250 nm to about 2,500 nm. In some embodiments, such as in any method described herein, wherein exposing the combination to a photon source comprises exposing the combination to a wavelength (e.g., photon) of about 300 nm to about 500 nm. In some embodiments, such as in any method described herein, wherein exposing the composition to a photon source results in decreased viscosity by at least 25%, and/or liquefaction of the composition.

In some embodiments, disclosed herein is a compound having a structure of Formula VI (shown in cis configuration as an example):

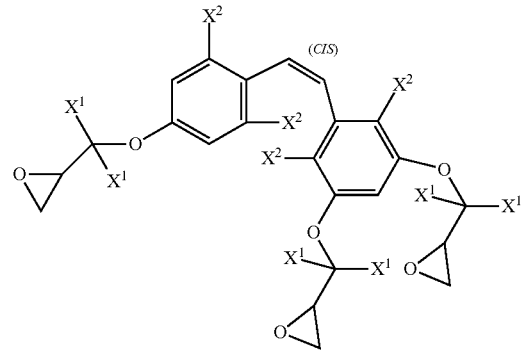

Formula VI

In some embodiments, a) each X$^1$ is independently CH$_3$ or H, b) each X$^2$ is independently selected from the group consisting of: H, F, a halomethyl (e.g., fluoromethyl such as CF$_3$), and CH$_3$, and c) the compound of Formula VI has a cis configuration (as indicated in the shown Formula VI). In some embodiments, each X$^1$ and X$^2$ are H.

In some embodiments, disclosed herein is a compound having a structure herein, such as of Formula VI, in a cis-to-trans mol ratio (e.g., around the center C=C or N=N moiety) of about 0:100 to about 100:0, such as about 1:99 to about 99:1, about 10:90 to about 90:10, about 5:95 to about 25:75, about 30:70 to about 70:30, or about 50:50. In some embodiments, disclosed herein is a compound having a structure herein, such as of Formula VI, in a cis-to-trans mol ratio (e.g., around the center C=C or N=N moiety) of about 1:99 to about 100:0, such as about 10:90 to about 100:0, about 20:80 to about 100:0, about 30:70 to about 100:00, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, disclosed herein is a compound having a structure of Formula V (shown in cis configuration as an example):

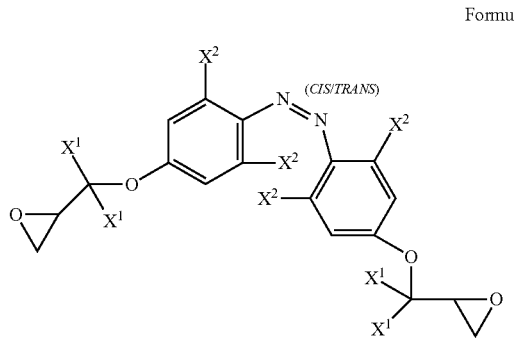

Formula V

In some embodiments, a) each $X^1$ is independently $CH_3$ or H; b) each X is independently selected from the group consisting of: H, F, a halomethyl (e.g., a fluoromethyl such as $CF_3$), and $CH_3$; and c) the Formula V structure has a cis or trans configuration (as indicated in the shown Formula V). In some embodiments, each $X^1$ is H and each $X^2$ is F.

In some embodiments, disclosed herein is a compound having a structure herein, such as of Formula V, in a cis-to-trans mol ratio (e.g., around the center N=N or C=C moiety) of about 0:100 to about 100:0, such as about 1:99 to about 99:1, about 10:90 to about 90:10, about 5:95 to about 25:75, about 30:70 to about 70:30, or about 50:50. In some embodiments, disclosed herein is a compound having a structure herein, such as of Formula V, in a cis-to-trans mol ratio (e.g., around the center N=N or C=C moiety) of about 1:99 to about 100:0, such as about 10:90 to about 100:0, about 20:80 to about 100:0, about 30:70 to about 100:00, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, disclosed herein, is a composition comprising a plurality of molecules, the plurality of molecules collectively comprising: a) at least one photo-isomerizable radical; b) at least one thermally reactive radical; and c) at least one thermally stable radical, wherein one or more photo-isomerizable radicals of the at least one photo-isomerizable radical optionally comprises one or more thermally stable radicals of the at least one thermally stable radical. In some embodiments, each photo-isomerizable radical comprise >X=Y<, wherein each X is independently C or N and each Y is independently C or N. In some embodiments, each photo-isomerizable radical is independently selected from the group consisting of an azo-benzene, a stilbene, an aromatic cyanoethene, a hemithioindigo, a pyrroline, and an isoindolinone. In some embodiments, each thermally stable radical independently is or comprises a substituted or unsubstituted aryl or substituted or unsubstituted heteroaryl. In some embodiments, each thermally reactive radical is independently selected from the group consisting of a hydroxyl, a thiol, an amine, an epoxide, cyanate ester, phthalonitrile, acetylene, maleimide, melamine, benzoxazine, amic acid, phenyl ethynyl, silanol, a silazane, a phosphoric acid salt, phosphoric acid ester, and phosphoric acid anhydride.

In some embodiments, i) all or some of the plurality of molecules, or ii) one or more photo-isomerizable radicals of the at least one photo-isomerizable radical, independently have a structure of Formula I:

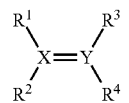

Formula I

In some embodiments, each X and Y are independently C or N; $R^1$ and $R^2$ are independently H, halo, cyano, substituted or unsubstituted aryl, or substituted or unsubstituted heteroaryl, or $R^1$ and $R^2$ are taken together to form a substituted or unsubstituted ring; and $R^3$ and $R^4$ are independently H, halo, cyano, substituted or unsubstituted aryl, or substituted or unsubstituted heteroaryl; and wherein at least one of $R^1$ or $R^2$ is not H, at least one of $R^3$ or $R^4$ is not H, and $R^1$, $R^2$, $R^3$, and $R^4$ are not all the same.

In some embodiments, i) all or some of the plurality of molecules, or ii) one or more photo-isomerizable radicals of the at least one photo-isomerizable radical, independently have a structure of Formula II:

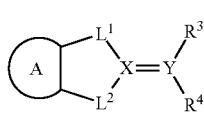

Formula II

In some embodiments, X is C; Y is C or N; $L^1$ and $L^2$ are independently a bond, —S—, —O—, amino, amide (lactam), alkylenyl, or carboxyl, wherein the ring comprising $L^1$ and $L^2$ is a 5 or 6 membered ring; and $R^3$ and $R^4$ are independently H, halo, cyano, substituted aryl or unsubstituted aryl, or substituted heteroaryl or unsubstituted heteroaryl; A is substituted aryl or unsubstituted aryl, or substituted heteroaryl or unsubstituted heteroaryl; and wherein at least one of $R^3$ and $R^4$ is not H; $R^3$, and $R^4$ are not all the same.

In some embodiments, all or a fraction of the molecules of the plurality of molecules independently have a structure of Formula III (shown in trans configuration as an example):

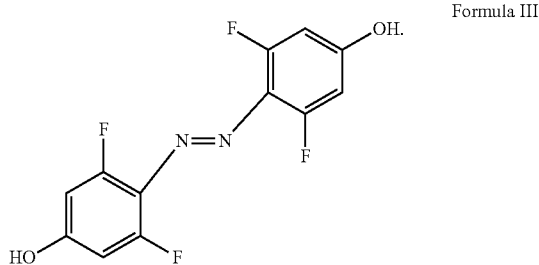

Formula III

In some embodiments, each structure of Formula III has a cis or trans configuration (e.g., around the center N=N or C=C moiety).

In some embodiments, one or more photo-isomerizable radicals of the at least one photo-isomerizable radical is an azo-benzene or a stilbene, or comprises a structure of Formula III in cis or trans configuration. In some embodiments, one or more thermally reactive radicals of the at least one thermally reactive radical is an epoxide. In some embodiments, one or more thermally stable radicals of the at least one thermally stable radicle is a substituted or unsubstituted benzene of an azo-benzene or a stilbene. In some embodiments, a) one or more photo-isomerizable radicals of the at least one photo-isomerizable radical is an azo-benzene, or a stilbene, or comprises a structure of Formula III or Formula IV; b) one or more thermally reactive radicals of the at least one thermally reactive radical is an epoxide; and c) one or more thermally stable radicals of the at least one thermally stable radicle is selected from a substituted or unsubstituted benzene of an azo-benzene or a stilbene. In some embodiments, the one or more photo-isomerizable radicals are in a cis-to-trans mol ratio of about 1:99 to about 100:0, such as about 10:90 to about 100:0, about 20:80 to about 100:0, about 30:70 to about 100:00, about 40:60 to about 100:0, about 50:50 to about 100:0, 10:90 to about 90:10, about 30:70 to about 70:30, about 5:95 to about 25:75, about 15:85 to about 30:70, or about 20:80. In some embodiments, such as in any composition described herein, the composition further comprises a reagent comprising one or more dianiline compounds.

DETAILED DESCRIPTION

Figure 1:
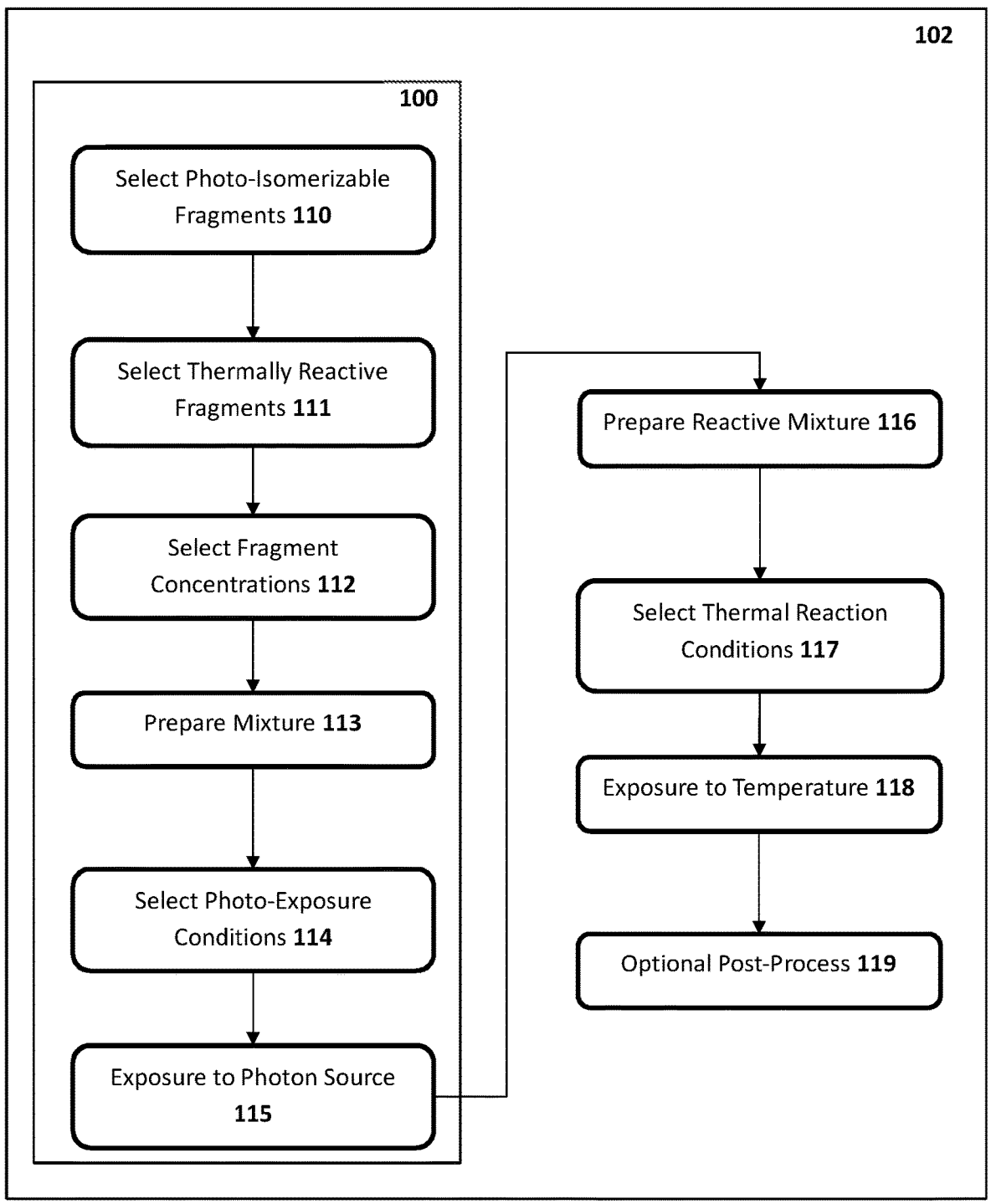
FIG. 1 illustrates an exemplary flow chart of a non-limiting example of a method for preparing a composition of matter provided herein, such as a resin, a cured resin, a prepreg, a composite, or the like, such as provided herein.

While various embodiments of the invention have been shown and described herein, it will be clear to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Throughout this application, various embodiments of this disclosure may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

"Amino" refers to the —NH2 radical.

"Cyano" refers to the CN radical.

"Nitro" refers to the NO2 radical.

"Oxo" refers to the =O radical.

"Hydroxyl" refers to the —OH radical.

"Alkyl" generally refers to a straight or branched hydrocarbon chain radical consisting solely of carbon and hydrogen atoms, such as having from one to fifteen carbon atoms (e.g., C1-C15 alkyl). Unless otherwise state, alkyl is saturated or unsaturated (e.g., an alkenyl, which comprises at least one carbon-carbon double bond).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n butylene, and the like.

"Aryl" refers to a radical derived from an aromatic monocyclic or multicyclic hydrocarbon ring system by removing a hydrogen atom from a ring carbon atom.

"Carbocyclyl" or "cycloalkyl" refers to a stable non aromatic monocyclic or polycyclic hydrocarbon radical consisting solely of carbon and hydrogen atoms, which includes fused or bridged ring systems, having from three to fifteen carbon atoms.

"Halo" or "halogen" refers to fluoro, bromo, chloro, or iodo radicals.

"Haloalkyl" refers to an alkyl radical, as defined above, that is substituted by one or more halogen radicals, as defined above.

The term "heteroalkyl" refers to an alkyl group as defined above in which one or more skeletal carbon atoms of the alkyl are substituted with a heteroatom (with the appropriate number of substituents or valencies—for example, —CH2- may be replaced with —NH— or —O—). For example, each substituted carbon atom is independently substituted with a heteroatom, such as wherein the carbon is substituted with a nitrogen, oxygen, sulfur, or other suitable heteroatom.

The term "Heterocyclyl" refers to a stable 3 to 18 membered non-aromatic ring radical that comprises two to twelve carbon atoms and from one to six heteroatoms selected from nitrogen, oxygen and sulfur.

The term "Heteroaryl" refers to a radical derived from a 5 to 10 membered aromatic ring radical that comprises a plurality of carbon atoms and one or more heteroatoms selected from nitrogen, oxygen and sulfur.

The compounds disclosed herein, in some embodiments, contain one or more asymmetric centers and thus give rise to enantiomers, diastereomers, and other stereoisomeric forms that are defined, in terms of absolute stereochemistry, as (R) or (S). Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.).

In some embodiments, a substituted group provided herein (e.g., substituted alkyl) is substituted by one or more substituent, each substituent being independently selected from the group consisting of halo, cyano, nitro, oxo, alkyl, haloalkyl, heteroalkyl, hydroxyl, alkoxy, ester, amide, aryl, heteroaryl, heterocycyl, or carbocycyl.

The terms "about" and "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, the terms can mean a range of up to 20%, up to 10%, up to 5%, or up to 1% of a given value. Alternatively, the terms can mean within an order of magnitude, preferably within 5-fold, and more preferably within 2-fold, of a value.

The terms "fragment" and "radical" refer to a part of a compound or molecule (e.g., component molecule described herein), such as in a composition (e.g., resin, prepreg, composite, or the like) provided herein. In various instances, a radical or fragment is an atom, part of a compound or molecule, or a compound or molecule itself. In certain instances, a fragment or radical is connected to one or more additional fragment or radical (e.g., to an additional radical or fragment described herein or to an —H, -halo, -alkyl, or the like), such as to form a compound or molecule, such as described herein. The terms "fragment" and "radical" are generally used interchangeably herein unless otherwise noted.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Provided in some embodiments herein is a composition of matter, and method for preparing the same, which provide the benefits of pre-reaction molecular configuration favoring high liquidity properties, and post-reaction configuration that favors mechanical strength, stiffness, and properties associated with high viscous and/or solid-state materials. In some embodiments, the composition of matter can comprise relaxing photo-isomerizable fragments, of which a fraction can be transformed from trans to cis configurations upon exposure to a photon source. In some embodiments, the composition of matter further comprises thermally reactive fragments, of which can enable thermal solidification of a mixture upon exposure to elevated temperatures. In some embodiments, a composition of matter can be combined with reinforcing additives to form a prepreg combination.

Composition of Matter

In some embodiments, provided herein is a composition of matter that comprises a photo-isomerizable fragment, a thermally reactive fragment, and a thermally stable fragment. In some embodiments, the composition comprises a plurality of molecules that collectively comprise a plurality of photo-isomerizable fragments, a plurality of thermally reactive fragments, and a plurality of thermally stable fragments. In some embodiments, the composition comprises a first component, wherein the first component comprises a plurality of first component molecules, each comprising a) a photo-isomerizable fragment; b) at least one thermally reactive fragment; and c) at least one thermally stable fragment. In some embodiments, the composition of matter further comprises a second component comprising a plurality of second component molecules, each comprising at least one thermally reactive fragment and at least one thermally stable fragment.

In some embodiments, the composition comprises a first component and a second component. In some embodiments, the first component comprises a plurality of first component molecules, each comprising a photo-isomerizable fragment. In some embodiments, the second component comprises a plurality of second component molecules, each comprising at least one thermally reactive fragment and at least one thermally stable fragment.

In some embodiments, the ratio of the number of thermally reactive fragments to the total number of molecules is at least 1:1, at least 2:1, or greater than 2:1, wherein the total number of molecules is based only on the composition, and does not include any associated solvent, diluent, or other processing aid. In some embodiments, a large ratio of thermally reactive fragments to the total number of molecules can result in the composition having a large molecular weight. In a non-limiting example, the composition can have a molecular weight of up to 165,000 g/mol. In some embodiments, the ratio of the number of photo-isomerizable fragments to thermally reactive fragments can range from 1:1000 to 10:1. In some embodiments, the ratio of the number of thermally stable fragments to the number of molecules ranges from 1:2 to 10:1.

In some embodiments, each photo-isomerizable fragment can be connected to H or at least one of another photo-isomerizable fragment, a thermally reactive fragment, and a thermally stable fragment. In some embodiments, each thermally reactive fragment can be connected to H or at least one of another thermally reactive fragment, a photo-isomerizable fragment, and a thermally stable fragment. In some embodiments, each thermally stable fragment can be connected to H or at least one of another thermally stable fragment, a photo-isomerizable fragment, and a thermally reactive fragment. In some embodiments, each photo-isomerizable fragment is a relaxing photo-isomerizable fragment.

In some embodiments, such as in any composition described herein, the first component or photo-isomerizable fragment, independently, comprises of a structure of Formula I:

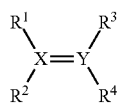

Formula I

In some embodiments, referring to Formula I, X and Y are independently carbon (C) or nitrogen (N) atoms. For example, both X and Y can be C, or either one of X and Y can C. Similarly, both X and Y can be N, or either one of X and Y can be N. In some embodiments, R is a Hydrogen atom (H), halo, a cyano group, a substituted aryl, an unsubstituted aryl, a substituted heteroaryl, or an unsubstituted heteroaryl. In some embodiments, $R^2$ is H, halo, a cyano group, a substituted aryl, an unsubstituted aryl, a substituted heteroaryl, or an unsubstituted heteroaryl. In some embodiments, $R^1$ and $R^2$ are taken together to form a substituted or unsubstituted ring. In some embodiments, at least one of $R^1$ and $R^2$ is not H. In some embodiments, $R^3$ is H, halo, a cyano group, a substituted aryl, an unsubstituted aryl, a substituted heteroaryl, or an unsubstituted heteroaryl. In some embodiments, $R^4$ is H, halo, a cyano group, a substituted aryl, an unsubstituted aryl, a substituted heteroaryl, or an unsubstituted heteroaryl. In some embodiments, at least one of $R^3$ and $R^4$ is not H. In some embodiments, $R^1$, $R^2$, $R^3$, and $R^4$ are not all the same. In some embodiments, a photo-isomerizable fragment is an azo-benzene, a stilbene, an aromatic cyanoethane, a hemithionindigo, a pyrroline, or an isoindolinone.

In some embodiments, such as in any composition described herein, the first component or photo-isomerizable fragment, independently, comprises of a structure of Formula IA:

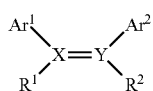

Formula IA

In some embodiments, referring to Formula IA, X and Y are independently carbon (C) or nitrogen (N) atoms. For example, both X and Y can be C, or either one of X and Y can C. Similarly, both X and Y can be N, or either one of X and Y can be N. In some embodiments, $R^1$ and $R^2$ are independently selected from a chemical bond to $Ar^1$ and/or $Ar^2$, H, and/or a cyano group. In some embodiments, $Ar^1$ and $Ar^2$ independently comprise a central ring system (Ar0), comprising an aromatic ring selected from benzene, naphthalene, anthracene, phenanthrene, pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, xanthene, benzofuran, isobenzofuran, dibenzofuran, benzothiophene, dibenzothiophene, benzoxazole, benzisoxazole, phenoxazine, benzothiazole, benzisothiazole, phenothiazine, and azulene, or any ring thereof in which one or more non-adjacent nitrogen or oxygen atoms in a ring is substituted by a carbonyl having a carbon as part of the ring, and chemically bonded combinations of the above (such as dithiophene, and thiophene-furan) having a total of 15 or fewer atoms selected from among C, N, O, and S. In some embodiments, each carbon not directly bonded to X or Y in Ar0 (central ring system) is independently bonded to an atom or group selected from among hydrogen, fluorine, chlorine, bromine, iodine, methyl, ethyl, n-propyl, iso-propyl, t-butyl, cyclopentyl, vinyl, ethynyl, allenyl, butadienyl, cyano, azo, carbonyl, imine, phenyl, and chemically stable combinations thereof (such as fluoromethyl, difluoromethyl, tribromomethyl), combinations in which an oxygen, nitrogen, or sulfur atom not part of the Ar0 (central ring system) forms a bridging bond between two carbon atoms bonded otherwise only to carbon or hydrogen atoms (for example, a methoxy substituted ring), and combinations including substitution for a hydrogen not in the Ar0 (central ring system) of any of the thermally reactive fragments (for example, a glycidyl group which comprises a methyl group with an epoxide group substituted for a hydrogen).

In some embodiments, one or more photo-isomerizable fragments (of any structural formula described herein) is present per molecule. In some embodiments, the fragments $Ar^1$ and Ar2 are linked by chemical bonds to one another.

In some embodiments, each thermally stable fragment comprises a substituted aryl, an unsubstituted aryl, a substituted heteroaryl, or an unsubstituted heteroaryl. In some embodiments, each thermally stable fragment is a substituted aryl, an unsubstituted aryl, a substituted heteroaryl, or an unsubstituted heteroaryl. In some embodiments, each thermally stable fragment comprises of multiple aryl (and/or heteroaryl) groups linked by one or more alkyl groups. In some embodiments, a thermally stable fragment is a substituted ring, or an unsubstituted ring, wherein the ring is selected from benzene, naphthalene, anthracene, phenanthrene, pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, xanthene, benzofuran, isobenzofuran, dibenzofuran, benzothiophene, dibenzothiophene, benzoxazole, benzisoxazole, phenoxazine, benzothiazole, benzisothiazole, phenothiazine, and azulene, or an aforementioned ring in which one or more non-adjacent nitrogen or oxygen atoms in a ring is substituted by a carbonyl having a carbon as part of the ring. In some embodiments, the thermally stable fragments can comprise chemically bonded combinations of the rings, wherein the number average of the total number of C, N, O, and S atoms per molecule exceed 15.

In some embodiments, each thermally reactive fragment is a hydroxyl, thiol, amine, epoxide, a cyanate ester, a phthalonitrile, an acetylene, a maleimide, a melamine, a benzoxazine, an amic acid, phenyl ethynyl, silanol, a silazane, a phosphoric acid salt, phosphoric acid ester, or phosphoric acid anhydride. In some embodiments, each thermally reactive fragment has a molecular weight of 50 g/mol to 500 g/mol. In some embodiments, each or some of the thermally reactive fragments can be chemically bonded to one or more photo-isomerizable groups within the same molecule. In some instances, the ratio of thermally reactive fragments to the total number of molecules is selected to enable solidification of the composition upon exposure to a selected temperature for a selected period of time. In some embodiments, said solidification of the composition can be based on cis configurations of the composition, due to exposure to a photo source. In some embodiments, thermally reactive fragments can be present as matched sets, for example, epoxide and amine groups. In some embodiments, thermally reactive fragments can require a catalyst to initiate bond formation.

In some embodiments, such as in any composition described herein, all or a fraction of the first component molecules have a structure of Formula I, wherein $R^1$ has a structure of $Ar^1$-$L^{1a}$-$Ar^{1a}$—$R^{1a}$; wherein $Ar^1$ is substituted aryl, unsubstituted aryl, substituted heteroaryl, or unsubstituted heteroaryl; $L^{1a}$ is a bond, —O—, amine, —S—, or carboxyl; Aria is substituted aryl, unsubstituted aryl, substituted heteroaryl, or unsubstituted heteroaryl; and $R^{1a}$ is H, a thermally reactive radical, or a linker-thermally reactive radical (e.g., wherein the linker is a —O—, —S—, alkyl, heteroalkyl).

In some embodiments, such as in any composition described herein, all or a fraction of the first component molecules have a structure of Formula I, wherein $R^2$ has a structure of $Ar^2$-$L^{2a}$-$Ar^{2a}$—$R^{2a}$; wherein $Ar^2$ is substituted aryl, unsubstituted aryl, substituted heteroaryl, or unsubstituted heteroaryl; $L^{2a}$ is a bond, —O—, amine, —S—, or carboxyl; $Ar^{2a}$ is substituted aryl, unsubstituted aryl, substituted heteroaryl, or unsubstituted heteroaryl; and $R^{2a}$ is H, a thermally reactive radical, or a linker-thermally reactive radical (e.g., wherein the linker is a —O—, —S—, alkyl, heteroalkyl).

In some embodiments, such as in any composition described herein, all or a fraction of the first component molecules have a structure of Formula I, wherein $R^3$ has a structure of $Ar^3$-$L^{3a}$-$Ar^{3a}$—$R^{3a}$; wherein $Ar^3$ is substituted aryl, unsubstituted aryl, substituted heteroaryl, or unsubstituted heteroaryl; $L^{3a}$ a bond, —O—, amine, —S—, or carboxyl; $Ar^{3a}$ is substituted aryl, unsubstituted aryl, substituted heteroaryl, or unsubstituted heteroaryl; and $R^{3a}$ is H, a thermally reactive radical, or a linker-thermally reactive radical (e.g., wherein the linker is a —O—, —S—, alkyl, heteroalkyl).

In some embodiments, such as in any composition described herein, all or a fraction of the first component molecules have a structure of Formula I, wherein $R^4$ has a structure of $Ar^4$-$L^{4a}$-$Ar^{4a}$—$R^{4a}$; wherein $Ar^4$ is substituted aryl, unsubstituted aryl, substituted heteroaryl, or unsubstituted heteroaryl; $L^{4a}$ a bond, —O—, amine, —S—, or carboxyl; $Ar^{4a}$ is substituted aryl, unsubstituted aryl, substituted heteroaryl, or unsubstituted heteroaryl; and $R^{4a}$ is H, a thermally reactive radical, or a linker-thermally reactive radical (e.g., wherein the linker is a —O—, —S—, alkyl, heteroalkyl).

In some embodiments, such as in any composition described herein, all or a fraction of the molecules the first component or photo-isomerizable fragment, independently have a structure of Formula II:

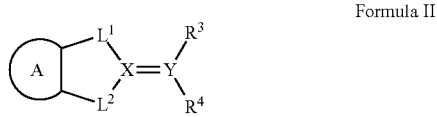

Formula II

In some embodiments, X can be C. In some embodiments, Y can be C or N. In some embodiments, $L^1$ can be a bond, —S—, —O—, amino, amide (lactam), alkylenyl, or carboxyl. In some embodiments, $L^2$ can be a bond, —S—, —O—, amino, amide (lactam), alkylenyl, or carboxyl. In some embodiments, a ring comprising $L^1$ and $L^2$ is a 5 or 6 membered ring. In some embodiments, $R^3$ can be H, halo, a cyano group, a substituted aryl, an unsubstituted aryl, a substituted heteroaryl, or an unsubstituted heteroaryl. In some embodiments, $R^4$ can be H, halo, a cyano group, a substituted aryl, an unsubstituted aryl, a substituted heteroaryl, or an unsubstituted heteroaryl. In some embodiments, A is a substituted aryl, an unsubstituted aryl, a substituted heteroaryl, or an unsubstituted heteroaryl. In some embodiments, at least one of $R^3$ and $R^4$ is not H. In some embodiments, $R^3$, and $R^4$ are not all the same.

In some embodiments, such as in any composition described herein, wherein all or a fraction of the molecules of the first component, independently have a structure of Formula III (shown in trans configuration as an example):

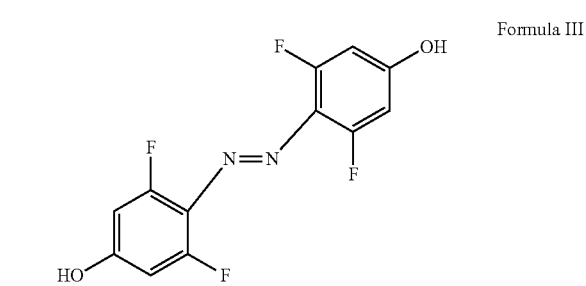 [SMILES: Oc1cc(F)c(/N=N/c2c(F)cc(O)cc2F)c(F)c1]

Formula III

In some embodiments, such as in any composition described herein, wherein all or a fraction of the molecules of the first component, independently have a structure of Formula IV (shown in cis configuration as an example):

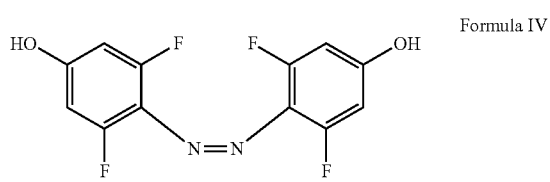 [SMILES: Oc1cc(F)c(/N=N\c2c(F)cc(O)cc2F)c(F)c1]

Formula IV

In some embodiments, such as in any composition described herein, one or more photo-isomerizable fragments of the photo-isomerizable fragments is an azo-benzene or a stilbene, or comprises a structure of Formula III or Formula IV. In some embodiments, such as in any composition described herein, one or more thermally reactive fragments of the thermally reactive fragments is an epoxide. In some embodiments, such as in any composition described herein, one or more thermally stable fragments of the thermally stable fragments is selected from a substituted or unsubstituted benzene of an azo-benzene or a stilbene. In some embodiments, such as in any composition described herein, a) one or more photo-isomerizable fragments of the photo-isomerizable fragments is an azo-benzene, or a stilbene, or comprises a structure of Formula III or Formula IV; b) one or more thermally reactive fragments of the thermally reactive fragments is an epoxide; and c) one or more thermally stable fragments of the thermally stable fragments is selected from a substituted or unsubstituted benzene of an azo-benzene or a stilbene.

In some embodiments, disclosed herein is a composition comprising a compound having a structure of Formula V (shown in cis configuration as an example):

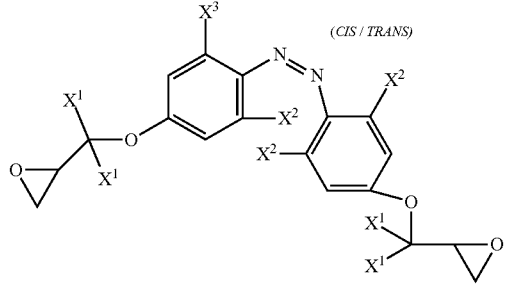

Formula V

In some embodiments, referring to Formula V, a) each $X^1$ is independently $CH_3$ or H; b) each $X^2$ is independently H, F, a halomethyl (e.g., a fluoromethyl such as $CF_3$), or $CH_3$; and c) the Formula V structure has a cis or trans configuration (as indicated in the shown Formula V). In some embodiments, referring to Formula V, each $X^1$ is H and each $X^2$ is F.

In some embodiments, disclosed herein is a composition comprising a compound having a structure herein, such as of Formula V, in a cis-to-trans mol ratio (e.g., around the center N=N or C=C moiety) of about 0:100 to about 100:0, such as about 1:99 to about 99:1, about 10:90 to about 90:10, about 5:95 to about 25:75, about 30:70 to about 70:30, or about 50:50. In some embodiments, disclosed herein is a composition comprising a compound having a structure herein, such as of Formula V, in a cis-to-trans mol ratio (e.g., around the center N=N or C=C moiety) of about 1:99 to about 100:0, such as about 10:90 to about 100:0, about 20:80 to about 100:0, about 30:70 to about 100:00, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, disclosed herein is a composition comprising a compound having a structure herein, such as of Formula V, wherein about 10 mol % to about 90 mol % of the photo-isomerizable radicals are in the cis configuration, and the remaining photo-isomerizable radicals are in the trans configuration. In some embodiments, disclosed herein is a composition comprising a compound having a structure herein, such as of Formula V, wherein about 5 mol % to about 25 mol % of the photo-isomerizable radicals are in the cis configuration, and the remaining photo-isomerizable radicals are in the trans configuration. In some embodiments, disclosed herein is a composition comprising a compound having a structure herein, such as of Formula V, wherein about 30 mol % to about 70 mol % of the photo-isomerizable radicals are in the cis configuration, and the remaining photo-isomerizable radicals are in the trans configuration. In some embodiments, disclosed herein is a composition comprising a compound having a structure herein, such as of Formula V, wherein about 1 mol % to about 99 mol % of the photo-isomerizable radicals are in the cis configuration, and the remaining photo-isomerizable radicals are in the trans configuration.

In some embodiments, disclosed herein is a composition comprising a compound having a structure of Formula VI (shown in cis configuration as an example):

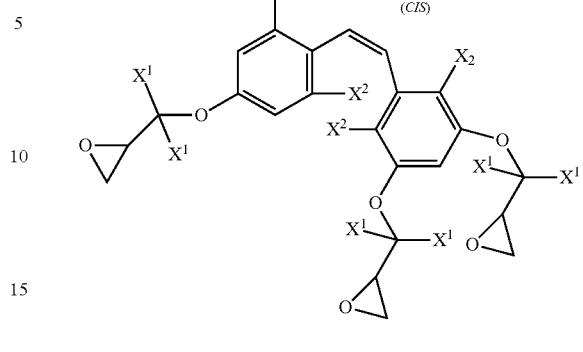

Formula VI

In some embodiments, referring to Formula VI, a) each $X^1$ is independently $CH_3$ or H, b) each $X^2$ is independently H, F, a halomethyl (e.g., fluoromethyl such as $CF_3$), or $CH_3$, and c) the Formula VI structure has a cis configuration (as indicated in the shown Formula VI). In some embodiments, referring to Formula VI, each $X^1$ and $X^2$ are H.

In some embodiments, disclosed herein is a composition comprising a compound having a structure herein, such as of Formula VI, in a cis-to-trans mol ratio (e.g., around the center C=C or N=N moiety) of about 0:100 to about 100:0, such as about 1:99 to about 99:1, about 10:90 to about 90:10, about 5:95 to about 25:75, about 30:70 to about 70:30, or about 50:50. In some embodiments, disclosed herein is a composition comprising a compound having a structure herein, such as of Formula VI, in a cis-to-trans mol ratio (e.g., around the center C=C or N=N moiety) of about 1:99 to about 100:0, such as about 10:90 to about 100:0, about 20:80 to about 100:0, about 30:70 to about 100:00, about 40:60 to about 100:0, about 50:50 to about 100:0, about 10:90 to about 90:10, about 30:70 to about 70:30, about 5:95 to about 25:75, about 15:85 to about 30:70, or about 20:80.

In some embodiments, disclosed herein is a composition comprising a compound having a structure herein, such as of Formula VI, wherein about 10 mol % to about 90 mol % of the photo-isomerizable radicals are in the cis configuration, and the remaining photo-isomerizable radicals are in the trans configuration. In some embodiments, disclosed herein is a composition comprising a compound having a structure herein, such as of Formula VI, wherein about 5 mol % to about 25 mol % of the photo-isomerizable radicals are in the cis configuration, and the remaining photo-isomerizable radicals are in the trans configuration. In some embodiments, disclosed herein is a composition comprising a compound having a structure herein, such as of Formula VI, wherein about 30 mol % to about 70 mol % of the photo-isomerizable radicals are in the cis configuration, and the remaining photo-isomerizable radicals are in the trans configuration. In some embodiments, disclosed herein is a composition comprising a compound having a structure herein, such as of Formula VI, wherein about 1 mol % to about 99 mol % of the photo-isomerizable radicals are in the cis configuration, and the remaining photo-isomerizable radicals are in the trans configuration.

In some embodiments, the composition comprising a structure of Formula V further comprises a reagent. In some embodiments, the reagent comprises one or more dianiline compounds. In some embodiments, the one or more dianiline compounds are independently selected from the group consisting of bis(4-aminophenyl)methane, bis(3-ethyl, 5-methy, 4-aminophenyl)methane, bis(3,3-diethyl, 4-aminophenyl)methane, meta-phenylenediamine, para-phenylenediamine, ortho-phenylenediamine, 4,4'-oxy-dianiline, 3,4'-oxy-dianiline, 3,3'-diaminodiphenylsulfone, 4,4'diaminodiphenulsulfone, 4,4'-Bis(3-aminophenoxy)diphenyl sulfone 4,4'-diaminodiphenylsulfide, 4,4'-(1,3-phenylenedioxy)dianiline, 4,4'-(9-fluorenylidene)dianiline, 4,4'-(hexafluoroisopropylidene)dianiline, 3,3'-(hexafluoroisopropylidene)dianiline, 4,4'-(1,1'-biphenyl-4, 4'-diyldioxy)dianiline, 4,4'-(4,4'-isopropylidenediphenyl-1, 1'-diyldioxy)dianiline, 4,4'-(Hexafluoroisopropylidene)bis(p-phenyleneoxy)dianiline, and any combination thereof.

In some embodiments, the composition comprising a structure of Formula VI further comprises a reagent. In some embodiments, the reagent comprises one or more dianiline compounds. In some embodiments, the one or more dianiline compounds are independently selected from the group consisting of bis(4-aminophenyl)methane, bis(3-ethyl, 5-methy, 4-aminophenyl)methane, bis(3,3-diethyl, 4-aminophenyl)methane, meta-phenylenediamine, para-phenylenediamine, ortho-phenylenediamine, 4,4'-oxy-dianiline, 3,4'-oxy-dianiline, 3,3'-diaminodiphenylsulfone, 4,4'diaminodiphenulsulfone, 4,4'-Bis(3-aminophenoxy)diphenyl sulfone 4,4'-diaminodiphenylsulfide, 4,4'-(1,3-phenylenedioxy)dianiline, 4,4'-(9-fluorenylidene)dianiline, 4,4'-(hexafluoroisopropylidene)dianiline, 3,3'-(hexafluoroisopropylidene)dianiline, 4,4'-(1,1'-biphenyl-4, 4'-diyldioxy)dianiline, 4,4'-(4,4'-isopropylidenediphenyl-1, 1'-diyldioxy)dianiline, 4,4'-(Hexafluoroisopropylidene)bis(p-phenyleneoxy)dianiline, and any combination thereof.

In some embodiments, the composition further comprises a reagent. In some embodiments, the reagent is selected from the group consisting of formaldehyde, acid chloride, alkyl chloride, alkyl bromide, alkyl iodide, metal hydroxide, aromatic cyanate ester, aromatic phthalonitrile, aryl amine, alkyl amine, or any combinations of two or more thereof. In some embodiments, the reagent comprises one or more dianiline compounds. In some embodiments, the one or more dianiline compounds are independently selected from the group consisting of bis(4-aminophenyl)methane, bis(3-ethyl, 5-methy, 4-aminophenyl)methane, bis(3,3-diethyl, 4-aminophenyl)methane, meta-phenylenediamine, para-phenylenediamine, ortho-phenylenediamine, 4,4'-oxy-dianiline, 3,4'-oxy-dianiline, 3,3'-diaminodiphenylsulfone, 4,4'diaminodiphenulsulfone, 4,4'-Bis(3-aminophenoxy)diphenyl sulfone 4,4'-diaminodiphenylsulfide, 4,4'-(1,3-phenylenedioxy)dianiline, 4,4'-(9-fluorenylidene)dianiline, 4,4'-(hexafluoroisopropylidene)dianiline, 3,3'-(hexafluoroisopropylidene)dianiline, 4,4'-(1,1'-biphenyl-4,4'-diyldioxy) dianiline, 4,4'-(4,4'-isopropylidenediphenyl-1,1'-diyldioxy) dianiline, 4,4'-(Hexafluoroisopropylidene)bis(p-phenyleneoxy)dianiline, and any combination thereof.

In some embodiments, the composition further comprises at least one additional component, for e.g., a third component for an aforementioned embodiment of the composition. In some embodiments, the additional component comprises at least one thermally stable fragment and at least one thermally reactive fragment. Non-limiting examples of said additional fragment include aromatic cyanate ester resins, such as Bispheol A dicyanate, Bisphenol E dicyanate, Bisphenol M dicyanate, novolac-based dicyanate (PT resin, PT-15, PT-30), Bisphenol S dicyanate, 4,4'-dicyanato-diphenyl ether, and resveratrol tricyanate. Other non-limiting examples of said additional fragment include aromatic phthalonitrile resins, such as Bisphenol A phthalonitrile, oligo(ether) phthalonitrile resins, and resveratrol phthalonitrile. Moreover, in some embodiments, said additional component includes combinations of any of the aforementioned aromatic cyanate ester resins and/or aromatic phthalonitrile resins. In some embodiments, said additional component includes oligomers of the aforementioned aromatic cyanate ester resins and/or aromatic phthalonitrile resins. In some embodiments, based on the parent phenols, said additional component includes incompletely converted versions of the aforementioned aromatic cyanate ester resins and/or aromatic phthalonitrile resins.

In some embodiments, the composition is a resin. In some embodiments, the composition is a resin additive. In some instances, the composition is flame-resistant.

In some embodiments, the composition (e.g., resin and/or prepreg composition (prepreg combination)—described further below) is configured on (e.g., one surface of) a substrate (e.g., comprising a first and second surface, such as wherein the composition is configured on one surface thereof), such as forming a kit (e.g., a prepreg tape). In some embodiments, the composition is detachably attached to the substrate (e.g., wherein the substrate comprises an adhesive on a surface thereof, such as to affix or facilitate the affixing of the composition to the substrate). In some embodiments, a kit, prepreg, or resin is used to repair an object (e.g., aircraft) or component there (e.g., a component of the fuselage of an airplane). In some embodiments, the substrate comprises an adhesive. In some embodiments, the substrate comprises a thermoplastic or an elastomer, with an optional polymer adhesive. In some embodiments, the substrate adhesive comprises one or more of the following: polyethylene terephthalate (Mylar) with a silicone elastomer pressure sensitive adhesive, polyethylene with an optional ethylene-propylene or EPDM pressure sensitive adhesive, polutetrafluororthtlene, fluorinated ethylene/propylene (FEP), or fluorinated silicone, polypropylene, polyamide, polyimide, polyvinyl chloride, polybutylene terephthalate, polyvinyl acetate, polyvinyl alcohol, cellulose, or polylactic acid. In some embodiments, the kit is a tape, such as comprising a composition (e.g., resin or prepreg) herein on a surface of a substrate, such as wherein the tape is in a rolled configuration. In certain embodiments, the composition is applied to a surface of an object (e.g., in need thereof), such as an aircraft or component thereof (e.g., wherein a kit comprises the composition, the composition being configured on a surface of a substrate, the composition being applied to the surface and being configured between the surface and the substrate following application). In some embodiments, the composition is applied to an aircraft or component thereof(e.g., in, into, or on a surface thereof) (e.g., wherein a kit comprises the composition, the composition being configured on a surface of a substrate, the composition being applied to the surface and being configured between the surface and the substrate following application). In some embodiments, the component comprises one or more (e.g., specific) surfaces, such as wherein the component and/or surface thereof comprises any one or more of the following: carbon fiber reinforced epoxy resin, glass fiber reinforced epoxy resin, carbon fiber reinforced bismaleimide resin, glass fiber reinforced bismaleimide resin, carbon fiber reinforced cyanate ester resin, glass fiber reinforced cyanate ester resin, carbon fiber reinforced phtalonitrile resin, glass fiber reinforced phthalonitrile resin, carbon fiber reinforced benzoxazine resin, glass fiber reinforced benzoxazine resin, carbon fiber reinforced polyimide resin, glass fiber reinforced polyimide resin.

In some embodiments, the composition can be provided in one or more packages. In some embodiments, the one or more packages is configured to contain the composition. In some embodiments, the composition may be configured as unmixed fragments. For example, non-limiting examples include photo-isomerizable fragments unmixed with thermally reactive fragments and thermally stable fragments, wherein the thermally reactive fragments and thermally stable fragments may or may not be mixed together. In some embodiments, unmixed fragments can be contained within separate compartments of the one or more packages. In some embodiments, each package of a plurality of packages can contain an unmixed fragment. In some embodiments, thermally reactive fragments and thermally stable fragments mixed together can be contained in the same compartment and/or package.

In some embodiments, the composition may be exposed to a photon source. In some embodiments, exposure to a photon source enables the photo-isomerizable fragments to undergo chemical rearrangement, or isomerization, to alter the shape of the molecules that contain them. As described further below, the dosage and wavelength of the photon exposure can be selected to obtain a specific chemical rearrangement of the composition. In some embodiments, photo-isomerizable fragments experience a rearrangement of selected chemical bonds upon exposure to radiation in the range of about 250 nm to 800 nm, (e.g., from about 300 nm to about 500 nm). In some embodiments, a photon dose ranges from 0.1 to 100 photons per photo-isomerizable fragment (e.g., 0.1 to 1 photons per photo-isomerizable fragment, 1 to 10 photons per photo-isomerizable fragment; 10 to 50 photons per photo-isomerizable fragment, 10 to 100 photons per photo-isomerizable fragment). In some embodiments, exposing the composition to a photon source results in a plurality of molecules acquiring an increase in heterogeneity in molecular shape, due to transformation of at least a fraction of the photo-isomerizable fragments present. For example, in some embodiments, exposure to a photon source transforms some or all of the photo-isomerizable fragments from trans to cis configurations. In some embodiments, between 10% to 90% of photo-isomerizable fragments in the composition may be transformed from trans to cis configuration, due to being exposed to a photon source. In some instances, increased number of molecules with cis configurations results in exemplary benefits such as decreased crystallization rates, decreased melting temperatures, and decreased viscosity (i.e. increased liquidity). In some instances, such transformation of the photo-isomerizable fragments decreases the viscosity of the composition mixture by at least 25% (e.g., about 25% to 90%), i.e. promotes the liquidity of the composition. In some embodiments, the thermally stable fragments transmit at least 90% of the intended frequency for photo-isomerization over a path length of cm.

Prepreg Combination (or "Prepreg Composition")

In some embodiments, the composition can be configured in a prepreg combination. In some embodiments, a prepreg combination comprises the composition and one or more reinforcing additives. In some embodiments, the composition comprise a fraction of molecules with cis transformations, after exposure to a photon source. In some embodiments, the composition in a prepreg combination is partially cured. In some embodiments, the composition is partially cured via exposure to a heat source. In some instances, thermal exposure to the composition increases the viscosity of the composition by at least 25%. In some embodiments, thermal exposure to the composition increases the viscosity of the composition from about 25% to about 1 trillion % (e.g., 25% to 75%, 100% to 1000%, 1000% to 10,000%, 100,000% to 1 million %, etc). In some embodiments, thermal exposure to the composition results in a chemical reaction from about 1% to about 70% of the thermally reactive groups In some embodiments, the reinforcing additive comprises reinforcing fibers. In some embodiments, the reinforcing fibers comprise glass fibers. As described herein, in some embodiments, the prepreg combination can be configured with a kit.

Cured Resin (E.g., Thermoset or a Thermoset Composite)

In some embodiments, a composition with cis transformations (after exposure to a photon source) further undergoes a thermal solidification process, wherein the composition can be partially or fully solidified by being exposed to elevated temperatures. In some embodiments, the thermally reactive fragments form chemical bonds upon exposure to elevated temperatures. In some embodiments, thermally reactive fragments are present as matched sets (for example, epoxide and amine groups). In some embodiments, thermally reactive fragments require a catalyst to initiate bond formation. In some instances, thermal fluctuations at the molecular level will act to return the cis configured photo-isomerizable fragments to a state of lower free energy over time in the absence of photo-isomerizing radiation. In some instances, these fluctuations result in further change to the shape of the photo-isomerizable fragments. For example, in some instances, the molecules with cis configuration can return to a trans configuration, i.e., the cis configuration can relax to the trans configuration, which in this example would be the lower energy state. In some instances, said fluctuations will take place at the same time in which the thermally reactive fragments act to form new chemical bonds to solidify the composition. In some instances, the chemically separate nature of photo-isomerizable fragments and thermally reactive fragments ensures that both are unchanged in their essential nature, such that isomeric change will continue to alter the molecular shape even during and after solidification by chemical reaction, while chemical reaction will continue even during and after alteration of molecular shape. In some instances, the approximate rates at which reaction and isomerization take place can be determined, thereby determining the correct initial proportions required for the composition.

In some instances, subjecting the cis transformed photo-isomerizable fragments to thermal exposure provides exemplary benefits during and after the time frame in which it occurs, such as the act of physical elongation at the molecular level, which will promote the formation of micro-voids and crazes. In some instances, such benefits from subjecting cis transformed photo-isomerizable fragments to thermal exposure do not need an external mechanical field, such that the composition of matter automatically endows an end-use article with the beneficial property.

In some instances, thermal exposure to the composition, which was subject to photon exposure and became more liquidity, results in an increase in viscosity. In some instances, thermal exposure to the composition increase the viscosity of the composition by at least 25%. In some embodiments, thermal exposure to the composition increases the viscosity of the composition from about 25% to about 1 trillion % (e.g., 25% to 75%, 100% to 1000%, 1000% to 10,000%, 100,000% to 1 million %, etc). In some instances, the percent of viscosity increase refers to the percent of thermally reactive fragments that have reacted. In some instances, the percent of viscosity increase refers to the percent of thermally reactive fragments not present in stoichiometric excess (for e.g., in systems with matched reactive fragments) that have reacted. In some embodiments, thermal exposure to the composition results in a chemical reaction from about 1% to about 70% (e.g., 1% to 10%, 10% to 50%, 25% to 55%) of the thermally reactive groups. In some embodiments, the composition will have between 1% to 100% (e.g., 5% to 95%, 25%-90%, etc.) of cis groups (cis configuration) converted to trans groups (trans configuration) upon completion of being subjected to thermal exposure. In some instances, thermal exposure to the composition achieves a range of solidification of at least 50% (e.g., 50%, 75%, 90%) solidification, by weight, through the thermal reaction. In some embodiments, thermal exposure of the composition results in an increase in mechanical strength and stiffness of the composition. In some embodiments, such exposure to elevated temperatures enables the composition to be cured or partially cured, thereby providing a cured or partially cured composition. In some embodiments, the cured composition is a cured resin. Reference to a cured resin, as described herein, shall refer to a fully cured resin and a partially cured resin interchangeably. In some instances, the cured resin is a thermoset and/or a thermoset composite. In some instances, the curing of the composition results in at least 25% curing of the composition. In some instances, the curing of the composition results in about 25% to about 90% curing of the composition. In some instances, the compositions, such as comprising the component parts and/or component parts in the amounts or ratios described herein, facilitate high curing capabilities of the compositions (e.g., resins and/or prepregs) provided herein.

In some embodiments, the composition is applied to a surface of an object, which can occur prior to being cured (or partially cured). In some embodiments, the composition is charged into a cast, which can occur prior to being cured (or partially cured).

In some embodiments, disclosed herein is a method and composition of matter which provide the benefits of pre-reaction molecular configuration favoring high liquidity properties, and post-reaction configuration that favors mechanical strength, stiffness and properties associated with high viscous and/or solid-state materials. In some embodiments, the pre-reaction molecular configuration comprises exposing the composition to a photon source. In some embodiments, the post-reaction configuration comprises exposing the composition, after exposure to a photon source, to a thermal source (e.g., heat source), so as to expose the composition to elevated temperatures. In some embodiments, such pre-reaction molecular configuration facilitate the preparation process for a cured resin (and/or prepreg combination), wherein a desired level of heterogeneity in molecular shape of a composition enables decreased crystallization rates, decreased melting temperatures, decreased viscosity (more liquidity), and potential speeding up reaction rates at lower temperatures. In some embodiments, the thermally reactive fragments enable for solidification of the composition that has such increased liquidity, via thermal exposure, thereby providing properties such as strength, stiffness, toughness, control of shrinkage and resistance to unwanted changes in dimension, decreased permeability leading to enhanced solvent resistance, resistance to oxidation, and resistance to moisture-induced degradation.

In some embodiments, the cured resin, prior to curing is combined with one or more reinforcing additives, wherein in some instances, a cured or partially cured thermoset composite is formed. In some embodiments, the one or more reinforcing additives comprise reinforcing fibers. In some embodiments, the one or more reinforcing fibers comprise glass and/or carbon fibers.

In some embodiments, the cured resin can be included with a kit, wherein the kit further includes one or more packages. In some embodiments, the one or more packages is configured to contain the cured resin.

In some embodiments, the kit can comprise a substrate, wherein the substrate can comprise of one or more of metal, ceramic, polymer, polymer-matrix composite, ceramic-matrix composite, or meta-matrix composite. In some embodiments, said substrate can include specific surfaces that can comprise of one or more of the following: carbon fiber reinforced epoxy resin, glass fiber reinforced epoxy resin, carbon fiber reinforced bismaleimide resin, glass fiber reinforced bismaleimide resin, carbon fiber reinforced cyanate ester resin, glass fiber reinforced cyanate ester resin, carbon fiber reinforced phthalonitrile resin, glass fiber reinforced phthalonitrile resin, carbon fiber reinforced benzoxazine resin, glass fiber reinforced benzoxazine resin, carbon fiber reinforced polyimide resin, glass fiber reinforced polyimide resin. In some embodiments, the cured resin is detachably affixed to said substrate of a kit. In some embodiments, said substrate comprises an adhesive. In some embodiments, said adhesive comprises a thermoplastic or an elastomer, with an optional polymer adhesive. In some embodiments, said adhesive comprises one or more of the following: polyethylene terephthalate (Mylar) with a silicone elastomer pressure sensitive adhesive, polyethylene with an optional ethylene-propylene or EPDM pressure sensitive adhesive, polutetrafluororthtlene, fluorinated ethylene/propylene (FEP), or fluorinated silicone, polypropylene, polyamide, polyimide, polyvinyl chloride, polybutylene terephthalate, polyvinyl acetate, polyvinyl alcohol, cellulose, or polylactic acid. In some embodiments, the kit is a repair kit. In some embodiments, the substrate may be in a rolled configuration. In some embodiments, the repair kit can be used in the aviation industry, such as on an aircraft.

In some embodiments, an article of manufacture comprises at least one component comprising the cured resin and/or a coating of the cured resin. In some embodiments, the article of manufacture is an aircraft. In some embodiments, a component of an article of manufacture comprises a substrate having the cured resin coated thereof. In some embodiments, the substrate can comprise of one or more of metal, ceramic, polymer, polymer-matrix composite, ceramic-matrix composite, or meta-matrix composite. In some embodiments, said substrate comprises a surface that comprises one or more of the following: carbon fiber reinforced epoxy resin, glass fiber reinforced epoxy resin, carbon fiber reinforced bismaleimide resin, glass fiber reinforced bismaleimide resin, carbon fiber reinforced cyanate ester resin, glass fiber reinforced cyanate ester resin, carbon fiber reinforced phthalonitrile resin, glass fiber reinforced phthalonitrile resin, carbon fiber reinforced benzoxazine resin, glass fiber reinforced benzoxazine resin, carbon fiber reinforced polyimide resin, glass fiber reinforced polyimide resin. In some embodiments, the cured resin is detachably affixed to said substrate. In some embodiments, said substrate comprises an adhesive. In some embodiments, said adhesive comprises a thermoplastic or an elastomer, with an optional polymer adhesive. In some embodiments, said adhesive comprises one or more of the following: polyethylene terephthalate (Mylar) with a silicone elastomer pressure sensitive adhesive, polyethylene with an optional ethylene-propylene or EPDM pressure sensitive adhesive, polutetrafluororthtlene, fluorinated ethylene/propylene (FEP), or fluorinated silicone, polypropylene, polyamide, polyimide, polyvinyl chloride, polybutylene terephthalate, polyvinyl acetate, polyvinyl alcohol, cellulose, or polylactic acid.

Method for Preparing Composition of Matter, Prepreg Combination, and Cured Resin FIG. 1 illustrates a non-limiting example of a method for preparing a composition 100, and a cured resin 102, wherein the composition comprises at least a fraction of molecules with cis configurations due to exposure from a photon source. In some embodiments, said method is completed in a batch process. In some embodiments, said method is completed in a continuous flow process. In some embodiments, said method is completed in a mixture of a batch process and continuous flow process.

In some embodiments, photo-isomerizable fragments are selected 110 for the composition and/or cured resin. In some embodiments, photo-isomerizable fragments are selected based on specific characteristics and properties desired for the composition and/or cured resin. Non-limiting examples of factors considered for selecting each photo-isomerizable fragment include i) the degree to which the photo-isomerization of the photo-isomerizable fragment imparts beneficial properties in the liquid state prior to solidification, ii) the degree to which the photo-isomerizable fragment imparts benefits in the solid state after thermally accomplished isomerization, iii) the times and temperatures selected for associated thermal solidification process and other related processes, iv) the times and temperatures selected for associated liquid-phase processes, and/or iv) optionally other production and performance considerations. In some embodiments, the identity of each fragment can be determined using any combination of the aforementioned non-limiting examples for selecting each photo-isomerizable fragment. In some embodiments, each selection of a photo-isomerizable fragment is part of a systematic optimization process, such that said selection may be subject to an iterative process. In some embodiments, selection of the photo-isomerizable fragments partly or fully coupled to selection of the thermally reactive fragments and thermally stable fragments in fixed ratios. In some embodiments, said fixed ratios is defined by available molecular structures.

In some embodiments, thermally reactive fragments are selected 111 for the composition and/or cured resin. In some embodiments, thermally reactive fragments are selected based on specific characteristics and properties desired for the composition and/or cured resin. Non-limiting examples of factors considered for selecting each thermally reactive fragment include i) the reaction rates of each thermally reactive fragment as a function of time, temperature, pressure, and/or the available concentrations of other reactive fragments; ii) the desired properties of the chemical structures formed during and after fragment reaction, and/or iii) optionally other production and performance considerations. In some embodiments, the identity of each fragment can be determined using any combination of the aforementioned non-limiting examples for selecting each thermally reactive fragment. In some embodiments, each selection of a thermally reactive fragment is part of a systematic optimization process, such that said selection may be subject to an iterative process. In some embodiments, selection of the thermally reactive fragments is partly or fully coupled to selection of the photo-isomerizable fragments and thermally stable fragments in fixed ratios. In some embodiments, said fixed ratios is defined by available molecular structures.

In some embodiments, selection of the thermally stable fragments is partly or fully coupled to the selection of the photo-isomerizable fragments and thermally reactive fragments in fixed ratios. In some embodiments, said fixed ratios are defined by available molecular structures.

In some embodiments, the photo-isomerizable fragments, the thermally reactive fragments, and/or the thermally stable fragments comprise a solid and/or liquid configuration. In some embodiments, each of the fragments comprise a single chemical compound, a pre-mixed set of chemical compounds, and/or a set of distinct chemical compounds or mixtures. In some embodiments, said chemical compounds are provided in the form of powders, pellets, granules, blocks, pastes, slurries, suspensions, emulsions, solutions, and/or other types of material forms.

In some embodiments, the desired concentrations of the photo-isomerizable fragments, thermally reactive fragments, and thermally stable reactants are selected 112 for the composition and/or cured resin. Non-limiting examples of factors considered for selecting the concentrations of each fragment include i) the desired rates of photo-conversion and reaction, ii) the times, temperatures and radiation intensities involved in processing, iii) the rates of thermal isomerization, iv) the beneficial properties achieved in both the liquid and solid states before and after solidification, respectively, v) volumetric density constraints, vi) mixing constraints, and/or vii) optionally other desired properties of the material (for e.g., thermoset, resin, prepreg combination) in the liquid and solid phase, as well as all processes involved. In some instances, a non-limiting example of a constraint relates to the density of the liquid phase of matter (for e.g., the composition, resin, and in some instances, may include a solvent), which can be nearly fixed. As such, in some instances, the sum of the densities of the photo-isomerizable, thermally reactive, and thermally stable fragments must match the density of the liquid phase under the respective process conditions. In some embodiments, each selection of a desired concentration for each fragment is part of a systematic optimization process, such that said selection may be subject to an iterative process.

In some embodiments, the concentration of the photo-isomerizable fragments ranges from 0.1 to 10 mmol per cubic centimeter. In some embodiments, the concentration includes the volume of composition and/or solvent. In some embodiments, the concentration of the total reactive fragments ranges from 0.1 to 10 mmol per cubic centimeter. In some instances, the thermally stable fragments are difficult to characterize by a molarity, due to being polymeric, and thus can be characterized by the respective density. As such, in some instances, the density of thermally stable fragments can be less than or equal to 2 g per cubic centimeter.

In some embodiments, the photo-isomerizable fragments, thermally reactive fragments, and thermally stable fragments are prepared 113 in an initial composition mixture. In some instances, the concentration for the different fragments is determined based on a specified weight or volume ratio as specified in the plurality of molecules mixed together. In some instances, the weight of the composition mixture ranges from 1 mg to 100,000 kg. In some embodiments, the different fragments are mixed together to achieve a degree of homogeneity, so as to be configured for the subsequent processing operations. In some embodiments, the initial composition mixture is further homogenized to achieve desired processing or end-use characteristics.

In some embodiments, one or more processing aids are added to the composition mixture to facilitate mixing or transport of the composition mixture, and/or to provide for desired product characteristics (for example, a controlled amount of porosity). In some embodiments, said processing aid comprises a chemical substance or a mixture of substances. In some embodiments, said processing aid comprises a liquid, a solid, a slurry, and/or any combination thereof. In some embodiments, said processing aid is a solvent, carrier fluid, a diluent or other type of medium. In some embodiments, said processing aid is configured to entrain or dissolve the composition mixture, thereby providing a fluid that is more readily transported, pumped, shaped, infused, and/or formed. In some embodiments, the proportion of solvent (processing aid) in a composition mixture ranges from 0.1% to 99.9% by weight. In some embodiments, one or more chemical reactions are performed to prepare the fragments for further processing.

In some embodiments, the conditions for photo-exposure of a composition mixture are selected 114. In some embodiments, photo-exposure conditions are selected based on specific characteristics and properties desired for the composition and/or cured resin. Non-limiting examples of factors considered in selecting photo-exposure conditions include i) the exposure dosage, intensity, and wavelength of photons provided, which can be based on the identity and concentrations of the photo-isomerizable fragments, thermally reactive fragments, and thermally stable fragments ii) the absorptivity characteristics of the system, iii) the desired processing characteristics such as throughput and final product state, and/or iv) other considerations relating to subsequent process or product characteristics. In some embodiments, an exposure dosage can range from 0.01 J to 1,000 J. In some embodiments, an exposure dosage can range from 0.1 photons to 100 photons per photo-isomerizable fragment. In some instances, the exposure dosage is measured by the composition as exposure wattage and residence time. In some embodiments, an intensity of the photo exposure ranges from 0.001 W per square centimeter to 1,000 W per square centimeter. In some embodiments, the wavelength of the photo exposure ranges from 250 to 2,000 nm. For example, in some embodiments, the wavelength of photo exposure range from 300 to 500 nm.

In some embodiments, the composition mixture is exposed 115 to the photons under the conditions selected. In some embodiments, exposure of the composition mixture to a photon source is through a continuous flow process, wherein the composition mixture is configured to flow at a predetermined flow rate. In some embodiments, exposure of the composition mixture to a photon source is through a batch process. In some embodiments, exposure of the composition mixture to a photon source is through a combination of a continuous flow process and batch process. In some embodiments, a monitoring mechanism is used to analyze and adjust parameters such as the cumulative radiation dosage, intensity, wavelength, temperature, pressure, flow rates and/or chemical compositions, in order to verify the correct execution of the intended process. In some embodiments, the monitoring mechanism is configured as a feedback controller. In some embodiments, exposure to a photon source transforms the photo-isomerizable fragments into a mixed state that decreases the homogeneity of their molecular geometric configurations. For example, in some embodiments, exposure to a photon source isomerizes some or all of the photo-isomerizable fragments from trans to cis configurations. In some embodiments, between 10% to 90% of photo-isomerizable fragments are transformed from trans to cis configuration due to being exposed to a photon source. In some instances, such isomerization and/or transformation of the photo-isomerizable fragments decreases the viscosity of the composition mixture by about 25% to 90%, i.e. promotes the liquidity of the composition mixture. In some embodiments, as the transformation and/or isomerization proceeds, processing aids (e.g., a solvent, diluent, etc.) included with the mixture preparation (see step 112) are removed if they become unnecessary. For example, a solvent and/or diluent added to decrease the viscosity of the composition mixture may no longer be required where the isomerization via photon exposure also decreases said viscosity. In some embodiments, such as in a batch process, said processing aids are removed through pot evaporation. In some embodiments, such as in a continuous flow process, said processing aids are removed through ultra-filtration. In some embodiments, one or more analytical examinations are undertaken to verify the formation of the intended reaction products at the intended concentrations.

In some embodiments, the composition mixture obtained from steps 110 through 115 of FIG. 1 provide an exemplary composition having a number of cis configured molecules via exposure to a photon source, as described herein. In some embodiments, the composition from step 115 can further be at least partially cured via a thermal curing process. In some embodiments, a partially cured composition mixture is combined with reinforcing additives to form a prepreg combination.

With continued reference to FIG. 1, in some embodiments, applying steps 116-118 enables the composition from step 115 to be partially or fully cured, thereby forming a cured resin as disclosed herein. In some embodiments, the composition obtained from step 115 is subsequently prepared for thermal exposure, wherein a thermal solidification reaction mixture (thermal reaction mixture) is prepared 116. In some embodiments, such preparation for thermal exposure can include any one or more of the following steps: i) transporting the liquid (composition from 115) to a location where thermal exposure takes place (for example, an oven), ii) removal of unstable, undesirable, or volatile components of the mixture, iii)) filling a cavity or mold with the composition, wherein the cavity or mold contains other components such as reinforcing fibers; iv) chemical reaction of the composition to alter its viscosity, stability, or otherwise impart needed properties, including the steps of optionally mixing the composition with other components, and v) further exposing the liquid (composition from step 115) to conditions of elevated or reduced pressure to facilitate flow, mixing, dissolution of components, and chemical reaction.

In some embodiments, the conditions for promoting a thermal reaction on the thermal reaction mixture (step 116) are selected 117. In some embodiments, thermal reaction conditions are selected based on specific characteristics and properties desired for the cured resin. In some embodiments, thermal reaction conditions include specifying exposure temperature(s) for the thermal reaction mixture, specifying the duration of time(s) for said exposure to the selected temperature(s), and/or specifying the pressure(s) to which the thermal reaction mixture is exposed to the selected temperatures. In some embodiments, atmospheric composition may be selected. Non-limiting examples of factors considered for selecting thermal reaction conditions include i) the composition of the thermal reaction mixture, ii) the geometry of said mixture, iii) the available rates of heat transfer, iv) the thermal characteristics of the reaction mixture, v) the thermal characteristics of supporting structures such as molds, the formation rate, and/or mass transport characteristics of reaction products, vi) the desired extent of chemical conversion, and/or vii) other process or product characteristics. In some embodiments, the reaction is carried out at temperatures ranging from 50° C. to 500° C. and/or pressures ranging from 0.1 psi to 1,000 psi. In some embodiments, the thermal reaction time can range from 1 s (second)

to 100 days. In some embodiments, the viscosity of the thermal reaction mixture prior to solidification ranges from 0.0001 Pa s to 1,000,000 Pa s. In some embodiments, the selection process is completed in a partial or iterative manner, adjusted during the reaction as determined by the observed characteristics of the process and/or materials involved. In some instances, the selection of the thermal reaction conditions are subject to constraints, such as the thermal and chemical stability of materials and/or the supply of energy.

In some embodiments, the thermal reaction mixture (116) is exposed to the thermal reaction conditions specified in 117, which can include a controlled sequence of temperatures, and/or other conditions as aforementioned. In some embodiments, the thermal reaction mixture undergoes partial or total solidification, via chemical reaction, once exposed to the thermal reaction conditions. In some embodiments, the thermal reaction mixture is exposed to the thermal reaction conditions through a batch process if total solidification of the thermal reaction mixture occurs. In some embodiments, wherein partial solidification of the thermal reaction mixture occurs, exposure to the thermal reaction conditions is through a batch process, a continuous flow process, or a combination of a batch process and continuous flow process. In some embodiments, a monitoring system indicates the current state of the process and verifies that the process has taken place as intended. In some embodiments, a control system enables deviations in the process from its intended state to be corrected. In some embodiments, a feedback controller is used. In some embodiments, a fluid container constrains the geometry of the thermal reaction mixture during at least part of the thermal solidification process. In some embodiments, following solidification, the container is separated from the solid object, formed by the thermal solidification process (118). In some embodiments, the quantity of the thermal reaction mixture thermally reacted in a single batch can range from 1 mg to 1,000 kg. In some instances, the thermal reaction mixture achieves a range of solidification of at least 50% solidification, by weight, through the thermal reaction. In some instances, the amount of solidification of the thermal reaction mixture is determined by an increase of viscosity to beyond 1,000,000 Pa s. In some embodiments, the composition will have between 1% to 100% (e.g., 5% to 95%, 25%-90%, etc.) of cis groups (cis configuration) converted to trans groups (trans configuration) upon completion of being subjected to thermal exposure.

In some embodiments, the thermal reaction product from 118 may be post-processed 119. Non-limiting examples of post-processing include applying a surface treatment or coating, laminating, surface grinding or finishing, cutting, shaping, hollowing, forming, pressing, machining, milling, lathing, fastening, adhering to other objects, crushing, pulverizing, and/or the like.

With continued reference to FIG. 1, in some instances, steps 110-114 are completed in any order, including simultaneously. In some embodiments, steps 110-114 must precede step 115, which must precede step 116. In some instances, steps 116 and 117 are completed in any order, including simultaneously. In some instances, step 117 is completed before, after, or simultaneously with any of steps 110-116. In some instances, steps 110-117 must precede step 118. In some instances, steps 110-118 must precede step 119.

System for Preparing a Composition and/or Cured Resin

Figure 2:
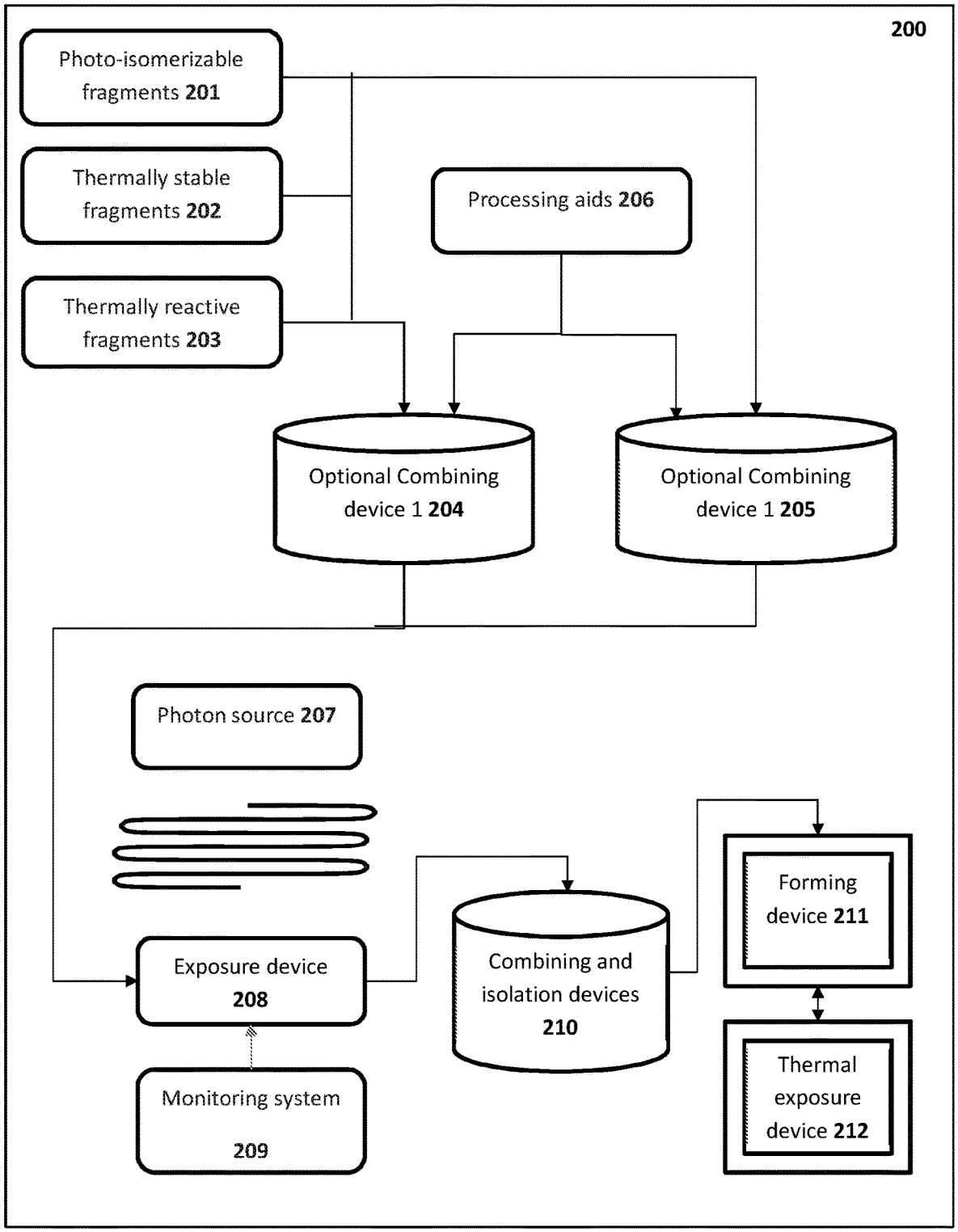
FIG. 2 illustrates an exemplary flow chart of a non-limiting example of a system and exemplary component parts, all or some of which optionally make up a system provided herein, for practicing a method provided herein.

FIG. 2 illustrates a non-limiting example of a flowchart depicting a system 200 for practicing the non-limiting example of a method disclosed in FIG. 1 for preparing a composition and cured resin disclosed herein. In some embodiments, photo-isomerizable fragments 201, thermally reactive fragments 202, and thermally stable fragments 203 are provided in the form of powders, pellets, granules, blocks, pastes, slurries, suspensions, emulsions, solutions, and/or other types of material forms. In some embodiments, the system 200 comprises containers, hoppers, spigots, piping, tubing, valves, and other appurtenances for containing and providing each of the fragments 201, 202, 203.

In some embodiments, the fragments 201, 202, 203 are combined in a first type of optional combining device 204. In some embodiments, processing aids 206 are also combined with the fragments within the first combining device 204, or prior to the fragments entering the first combining device 204. In some embodiments, the first combining device 204 can be configured to contain the fragments 201, 202, 203, and optionally processing aids 206 in a controlled mixture. In some embodiments, the first combining device 204 comprises one or more static mixers, fluid dynamic mixers, mixing heads, mixing containers, mixing blades, instrument ports, instruments, motors, tubing, piping, valves, and other appurtenances needed for containing and providing the composition mixture. In some embodiments, the first combining device 204 has a batch capacity from 1 ml to 100,000 L. In some embodiments, the first combining device 204 has a flow capacity from 1 ml to 1,000 L per minute.

In some embodiments, the fragments 201, 202, 203 are combined in a second type of optional combining device 205. In some embodiments, the system 200 can include either one of the first combining device 204 and second combining device 205, or both. In some embodiments, processing aids 206 are also combined with the fragments within the second combining device 205, or prior to the fragments entering the second combining device 205. In some embodiments, the second combining device 205 is configured to provide the fragments 201, 202, 203 and optionally, processing aid 206, in a form suited for photon exposure and subsequent operations, by combining the chemical substances comprising the fragments 201, 202, 203 and optional processing aid 206 into a controlled mixture, and allowing for an optional chemical transformation. In some embodiments, the second combined device 205 comprises one or more static mixers, fluid dynamic mixers, mixing heads, mixing containers, mixing blades, fluidic reactors, reaction vessels, gas removal apparatus, instrument ports, monitoring instruments, motors, tubing, piping, valves, and other appurtenances needed for containing and providing the composition mixture. In some embodiments, the second combining device 205 has a batch capacity from 1 ml to 100,000 L. In some embodiments, the second combining device 205 has a flow capacity from 1 ml to 1,000 L per minute.

In some embodiments, the processing aids 206 comprise a chemical substance or mixture of substances configured to entrain or dissolve the fragments 201, 202, 203, thereby providing a fluid that is more easily transported, pumped, shaped, infused or formed. In some embodiments, the processing aids 206 is a liquid. In some embodiments, the processing aids 206 can be a solvent, diluent, and/or other type of medium. In some embodiments, the processing aids 206 is provided in a quantity from 1 mg to 100,000 kg. In some embodiments, the processing aids 206 can comprise one or more chemical substances, which, in some instances, can be dissolved or finely dispersed. In some embodiments, the processing aids 206 react with one or more of the chemical compounds in the mixture of the fragments 201, 202, 203 contained in the first combining device 204 and/or second combining device 205. In some embodiments, the processing aids 206 react with one or more of the chemical compounds in the mixture of the fragments 201, 202, 203 prior to entering the first and/or second combining device 204, 205. In some embodiments, the system comprises containers, hoppers, spigots, piping, tubing, valves, and other appurtenances required to contain and provide the processing aids 206.

In some embodiments, the system 200 comprises a photon source 207 configured to provide a selected intensity of radiation to an exposure device 208. In some embodiments, the photon source 207 is stationary, while the exposure device 208 comprises piping, tubing, and appurtenances for transporting a fluid through the exposure device 208 in a controlled fashion. In some embodiments, the photon source 207 comprises a moveable lamp or terminus of an optical cable that is moved in a prescribed fashion around a stationary exposure device 208. In some embodiments, the photon source 207 can comprise an array of LEDs, fiber optics, lasers, and/or lamps. In some embodiments, the photon source 207 and exposure device 208 also comprise containers, static or fluid mixing equipment, instrument ports, separation apparatus, motors, valves, and/or other required accessories. In some embodiments, the photon source 207 and exposure device 208 are comingled or joined to form a single operational unit. In some embodiments, the system 200 further comprise a monitoring system 209 configured for feedback and control of the process by recording or displaying information about current, past, or planned radiation intensities at selected wavelengths, along with, optionally, other process conditions. In some embodiments, the photon source 207 provides photons at the rate of 0.1 W to 10,000 W. In some embodiments, the exposure device 208 has a batch capacity from 0.1 mL to 100 L. In some embodiments, the exposure device 208 can have a flow capacity from 0.1 mL per minute to 100 L per minute.

In some embodiments, the system can comprise combining and isolation devices 210 for preparing the composition obtained from the exposure devices 208 for thermal solidification reaction operations. In some embodiments, the combining and isolation devices 210 can comprise filters, membrane separators, gravimetric separators, distillation apparatus, sedimentation or settling equipment, melting equipment, mixing equipment, particle size selection equipment, dissolved gas removal equipment, pouring equipment, or other equipment and accessories as selected by those skilled in the art of thermal solidification reaction operations. In some embodiments, the combining and isolation devices 210 have a batch capacity from 1 ml to 100,000 L. In some embodiments, the combining and isolation devices 210 have a flow capacity from 1 ml to 1,000 L per minute.

In some embodiments, the system can comprise forming devices 211 and thermal exposure devices 212 configured for performing thermal solidification of the reaction mixture obtained from the combining and isolation device 210. In some embodiments, the forming devices 211 can comprise open molds, closed molds, open containers, and/or tool surfaces. In some embodiments, articles intended for joining and bonding to the solidified material, such as inlaid reinforcements, inlaid sensors, or temporary support structures, are placed within the forming device prior to the introduction of the reaction mixture received from the combining and isolation devices 210. In some embodiments, the forming devices 211 comprise equipment for processing after thermal exposure is complete, such as cutting, sanding, coating, or bonding equipment. For example, in some instances, the thermal reaction mixture can be partially cured through thermal exposure from the thermal exposure device 212, further processed (e.g., processed into a prepreg, cast, coat, etc.) via the forming devices 211 or other devices, and subsequently fully cured via the thermal exposure device 212. In some embodiments, the thermal exposure devices 212 comprise ovens, pressurized ovens, electrical and/or magnetic heating systems, forced air convective heating systems, and/or radiant heating systems. In some embodiments, the forming devices 211 and thermal exposure devices 212 further comprise accessories such as valves, tubing, support plates, cull plates, bleeder layers, sealants, tapes, breather films, release films, pumps, instrument ports, measuring instruments, documentation, diagrams, and other materials required for safe and efficient operation. In some embodiments, the forming device 211 and/or thermal exposure device 212 have a batch capacity from 1 ml to 100,000 L. In some embodiments, the forming device 211 and/or thermal exposure device 212 have a flow capacity from 1 ml to 1,000 L per minute.

EXAMPLES

Example 1—Synthesis of Compound Having Photo-Isomerizable, Reactive, and Thermally Stable Fragments Chemical Synthesis of precursors: Reference is made to the method reported by Bléger et al. in "o-Fluoroazobenzenes as Readily Synthesized Photoswitches Offering Nearly Quantitative Two-Way Isomerization with Visible Light", appearing in J. Am. Chem. Soc. 2012, Vol. 134, pp. 20597-20600, with supporting information followed.

Solvents and starting materials are used as received. Reactions are monitored by thin layer chromatography (TLC) on silica gel plates (Merck 60F-254) using a Merck MC1125370001 254 nm ultraviolet (UV) lamp. Column chromatography is performed using Silica gel (Merck 60, particle size 0.040-0.063 mm). Nuclear magnetic resonance (NMR) spectra are obtained with the aid of a Bruker 300 MHz (75 MHz for 13C) spectrometer using residual protonated solvent signals as the internal standard (1H-NMR: δ (CDCl3)=7.26 ppm, δ (DMSO-d6)=2.50 ppm and 13C-NMR: δ (CDCl3)=77.16 ppm, δ (DMSO-d6)=39.52 ppm).

Synthesis of 2,6-difluoro-4-iodoaniline: To a solution of 2,6-difluoroaniline (2.15 g, 17 mmol, ≥97%, from Sigma-Aldrich) and para-toluene sulfonic acid monohydrate (p-TsOH, 0.76 g, 4 mmol, ReagentPlus ≥98%, from Sigma-Aldrich) in dimethylformamide (DMF, 35 mL, ACS Reagent ≥99.8%, from Sigma-Aldrich) in a 250-mL glass Erlenmeyer flask is added dropwise N-iodo-succinimide (NIS, 4.95 g, 22 mmol, "for synthesis" grade from Sigma-Aldrich) dissolved in DMF (25 mL) at 5° C. The mixture is stirred for 2.5 hours at room temperature using a Teflon-coated disposable magnetic stir bar (Fischer Scientific #14-513-95) and stir plate (Corning™ Product #6796420D). Then the mixture is diluted with 100 mL ethyl acetate (ACS Reagent, ≥99.5%, from Sigma-Aldrich) and transferred to a 500-mL glass separatory funnel. In the funnel the mixture is thoroughly washed with a saturated solution of sodium chloride (anhydrous, Redi-Dri™, free-flowing, ACS reagent, ≥99%, from Sigma-Aldrich) in de-ionized water. The two phases are allowed to separate by coalescence and the aqueous phase is then drained from the funnel. The remaining organic phase is transferred to a clean 250-mL Erlenmeyer flask, to which portions of 5-10 g of magnesium sulfate (anhydrous, Reagent Plus, ≥99.5%, from Sigma-Aldrich) are added. The flask is occasionally swirled and the powder observed periodically. Portions are added until the powder is observed to be free flowing rather than clumped. Then the contents of the flask are passed through a suction-assisted filtration device using a Whatman Grade 4 filter paper fitted to the device. The filtrate is then transferred to a rotary evaporator capable of reduced pressure operation (Büchi® Rotavapor R-100), wherein evaporation of the solvent leads to the formation of a brown solid, the aforementioned 2,6-difluoro-4-iodoaniline in a quantity of about 5 g. This procedure is repeated five times and the five batches of the aforementioned 2,6-difluoro-4-iodoaniline are combined into a single thoroughly mixed 25 g batch of solid material.

Synthesis of 2,2',6,6'-tetrafluoro-4,4'-diiodoazobenzene: A 1-L glass Erlenmeyer flask in a thermostatically controlled water bath (Julabo PURA 10) is charged with 25 g (100 mmol) of the 2,6-difluoro-4-iodoaniline as obtained from the previous step and a freshly ground mixture of potassium permanganate (50 g, ACS Reagent, ≥99%, from Sigma-Aldrich) and iron(ii) sulfate heptahydrate (50 g, ACS Reagent, ≥99.0%, from Sigma-Aldrich) dissolved in dichloromethane (400 mL, puriss. Grade, ≥99%, from Sigma-Aldrich). The solution is stirred while the temperature is maintained at 20° C. for 2 days. The solution is then divided into portions of approximately 20 mL each, and each portion is filtered through roughly 5 g diatomaceous earth (Celite® S from Sigma-Aldrich) placed in the bottom of a 50-mL syringe. The portions are collected in a 1-L Erlenmeyer flask, to which portions of approximately 10 g of magnesium sulfate are added, and observed with occasional swirling. Portions are added until the powder is observed to flow freely, then the mixture is passed through a suction-assisted filtration device using a Whatman Grade 4 filter paper fitted to the device. The filtrate is then transferred to a rotary evaporator capable of reduced pressure operation (Büchi® Rotavapor R-100), wherein evaporation of the solvent leads to the formation of a crude solid (2-5 g). The solid is then divided into ten portions of around 200-500 mg each, each portion is dissolved in 200-500 mL of an equal mixture by volume of dichloromethane and hexanes (HPLC Plus grade, ≥98.5%, from Sigma-Aldrich), and injected into the chromatography column. The fractions passing through the column are then analyzed via NMR as described previously and those fractions containing the 2,2',6,6'-tetrafluoro-4,4'-diiodoazobenzene are retained. The retained solutions are transferred in multiple batches to a rotary evaporator capable of reduced pressure operation (Büchi® Rotavapor R-100), wherein evaporation of the solvent leads to the formation of a red-orange solid, the aforementioned 2,2',6,6'-tetrafluoro-4,4'diiodoazobenzene, with a total of 2-3 g recovered. If the total recovered is less than 2.5 g, the synthesis is repeated until a total of at least 2.5 g is obtained. If multiple synthesis batches are produced, all batches are combined into a single solid batch and mixed thoroughly.

Synthesis of compound having photo-isomerizable, reactive, and thermally stable fragments: Reference is made to methods specified by Yang et. al. in "Highly Efficient Synthesis of Phenols by Copper-Catalyzed Hydroxylation of Aryl Iodides, Bromides, and Chlorides" appearing in Organic Letters, 2011, Vol. 13, pp. 4340-4343.

Synthesis of 2,2',6,6'-tetrafluoro-4,4'-dihydroxyazobenzene: A 100-mL freshly flame-dried glass Erlenmeyer flask with a clean, dried Teflon-coated magnetic stir bar (Fisher Scientific item #14-513-93) is charged with copper(I) iodide (0.188 g, 0.988 mmol, "for synthesis" grade, from Sigma-Aldrich) and 8-hydroxyquinoline N-oxide (ligand L5, per the nomenclature of the aforementioned publication by Yang et al., 0.637 g, 3.96 mmol, 98%, from Sigma-Aldrich). The flask is sealed, evacuated, and then backfilled with an argon atmosphere. Under argon atmosphere, 2.50 g (4.94 mmol, or 9.88 mmol eq. I) of the 2,2',6,6'-tetrafluoro-4,4'-diiodoazobenzene obtained by the aforementioned precursor synthesis and 10 mL dimethyl sulfoxide (DMSO, puriss. p. a., ACS Reagent grade, ≥99.9%, from Sigma-Aldrich) purchased and subsequently dried by the addition of portions of roughly 0.1% of the weight of solvent to be dried of calcium hydride ("for synthesis" grade, from Sigma-Aldrich). The flask is then stirred by means of an external magnetic stir plate (Corning™, Product #6796420D). Following this, cesium hydroxide monohydrate (0.498 g, 2.97 mmol, 99.95% trace metals basis, from Sigma-Aldrich) and 10 mL distilled water is added. The temperature is increased to 100° C. while the mixture stirs. Every 6 to 12 hours, a roughly 0.1 mL sample of the reaction mixture is removed from the flask under argon atmosphere and tested using thin layer chromatography as described in the general procedures for synthesis of precursors. Once the thin layer chromatography test reveals the complete disappearance of the initial reactants, the reaction is stopped. Typically the stopping point is reached in 24-48 hours.

Once the stopping point is reached, the heat is turned off and the reaction mixture allowed to cool to ambient temperature naturally. Upon reaching ambient temperature, 1 mL portions of 0.1 M aqueous hydrochloric acid (available from Sigma-Aldrich as a pre-mixed solution as "endotoxin free" grade) are added and the solution pH checked with a pH indicator paper or probe (for example, Fisher Scientific product #09-876-17) until the pH reaches a stable value less than 7. Following this, 50 mL of ethyl acetate (ACS Reagent, ≥99.5%, from Sigma-Aldrich) is added. The solution is divided into two roughly equal portions, each of which is filtered through roughly 5 g diatomaceous earth (Celite® S from Sigma-Aldrich) placed in the bottom of a 50-mL syringe. The filtrate is collected in a 500-mL glass Erlenmeyer flask, and washed with 200 mL of ethyl acetate. The resulting organic extracts are concentrated by transferring the organic solution to a rotary evaporator capable of reduced pressure operation (Büchi® Rotavapor R-100) until approximately 80 mL of organic solution remains. This solution is divided into portions of roughly 50 mL each, and each portion is passed through a 0.45-micron Teflon filter (Whatman Puradisc 25) attached to a glass syringe. The filtrate is collected in a clean 100-mL glass Erlenmayer flask, then injected into a freshly prepared chromatography column (Silica gel (Merck 60, particle size 0.040-0.063 mm, prepared with ethyl acetate). The fractions passing through the column are then analyzed via NMR as described previously and those fractions containing the 2,2',6,6'-tetrafluoro-4,4'-dihydroxyazobenzene are retained. The retained solutions are transferred in multiple batches to a rotary evaporator capable of reduced pressure operation (Büchi® Rotavapor R-100), wherein evaporation of the solvent leads to the formation of a solid or oil, the aforementioned 2,2',6,6'-tetrafluoro-4,4'-dihydroxyazobenzene, in an expected amount of 1.5-2.5 g. If the total recovered is less than 2.0 g, the synthesis is repeated until a total of at least 2.0 g is obtained. If multiple synthesis batches are produced, all batches are combined into a single batch and mixed thoroughly.

Example 2: Photo-Isomerization of Mixture

A Unigsys FlowSyn reaction system is assembled with the following components: PhotoSyn reactor with 260 1-W 455 nm LEDs (along with blue/green/white variable wavelength LED replacement), UQ1053 Polar Bear Plus temperature control unit, UQ1063 pump with pressure transducer, UQ1100 flow UV spectrophotometer, UQ1102 flow cell and optical fibers for spectrophotometer, FlowControl software, and UQ9500 logging kit for PC. The flow path is designed so that fluid passes from a feed bottle, through the pump, then the temperature control unit, then the reactor, and then the spectrophotometer before being collected in a receiving bottle. The software is installed on a Dell Inspiron 17 7000 series laptop connected to the unit. In a clean large glass bottle (200-mL marked capacity from the Uniqsis UQ6000 bottle kit), 200-mL of ethyl acetate (ACS Reagent, ≥99.5%, from Sigma-Aldrich) is added. The bottle, along with a second clean, empty receiving bottle, is connected to the reaction system. The pump, temperature control unit, and spectrophotometer are started, and the system is purged with ethyl acetate at a flow rate of 20 mL/min. for 10 minutes at a temperature of 20° C., while a baseline UV-Vis spectrum is collected.

In a clean large glass bottle (200-mL marked capacity from the Uniqsis UQ6000 bottle kit, with closure removed) is placed 2.0 g of the 2,2',6,6'-tetrafluoro-4,4'-dihydroxyazobenzene, prepared as described previously, to which is added 200 mL of ethyl acetate (ACS Reagent, ≥99.5%, from Sigma-Aldrich) and a Teflon-coated disposable magnetic stir bar (Fischer Scientific #14-513-95). A temporary cap is placed on the bottle and the bottle is placed on a stir plate (Corning™, Product #6796420D). The mixture is stirred at room temperature for 10 minutes, or until complete dissolution is noted. The temporary cap and stir bar are removed, and the matching special closure from the UQ6000 kit is placed on the bottle. The bottle is then connected to the assembled Uniqsis reaction system in place of the ethyl acetate feed. The receiving bottle is replaced with an empty bottle and re-connected to the system. The cooling unit is engaged and the pressure adjusted to maintain a flow rate of 20 mL/min. The optical output power is adjusted to 15 W. These conditions are maintained for approximately 10 minutes (or until all but 5 mL of the feed fluid is consumed if the flow rates are adjusted during the procedure) while the spectrophotometer records the spectrum of material passing through. Per the description and data for a number of substantially similar chemical compounds provided by Bléger et al., p. 20598-20599, one skilled in the art of interpreting ultraviolet-visible light spectra determines the ratio of azobenzene isomers produced on a continuous basis, and by means of adjusting pressures and optical power intensities, ensures that photo-conversion of 70 mol % of the trans (E) isomer to cis (Z) isomer takes place. In the event that the blue light source provides inadequate conversion, the variable wavelength LED is optionally substituted and the wavelength adjusted to provide more selective irradiation of the trans isomer. In the event that more than 70% photo-conversion cannot be avoided, a portion of the starting solution is withheld from the process and added to the receiving bottle once the process is complete, so as to dilute the quantity of photo-converted material appropriately. One skilled in the art of solution blending determines the appropriate quantity to withhold by means of an algebraic formula involving the observed photo-conversion of material passed through the reaction system.

The photo-converted material is concentrated by applying vacuum after transferring the solution to a reduced pressure rotary evaporator (Büchi® Rotavapor R-100) shielded from ambient light, until the amount of solvent recovered reaches about 200 mL. The concentrated material may form co-crystals or remain as a viscous oil, however the presence of a 70:30 mixture provides a eutectic effect that lowers the melting point of any co-crystals. If needed, the melting point of the mixture after concentration is determined by one skilled in the art of measurement with an Omega MPS10-240 melting point apparatus.

Example 3—Preparation of Curative Mixture and Curing of the Mixture

Preparation of curative mixture: In a 40-mL glass scintillation vial (wrapped in aluminum foil to shield it from light) with Teflon-lined cap is placed 1.96 g of the aforementioned 2,2',6,6'-tetrafluoro-4,4'-dihydroxyazobenzene mixture prepared as previously described. If the melting temperature of the mixture is below 50° C., the mixture is heated to 10° C. above the melting temperature. Otherwise, 0.5 g portions of ethyl acetate (ACS Reagent, ≥99.5%, from Sigma-Aldrich) are added with the vial sealed tightly until the mixture is liquid at 60° C. A disposable Teflon-coated stir bar (Fischer Scientific #14-513-93 is added). The bottle is placed on a stir plate (Corning™, Product #6796420D) while the temperature is maintained at 60° C., while the contents are stirred. Once any solids are dissolved or melted, 0.0533 g of copper(II) acetyletonate (CuAcAc, (for chemical synthesis" grade, from Sigma-Aldrich) is added. Stirring is continued until all contents are dissolved. If necessary, portions of 0.5 g ethyl acetate are added to achieve complete dissolution.

In a separate open 200-mL glass container (wrapped in aluminum foil to shield it from light), 75 g of Primaset LECy (as-received, from Novoset, maintained below 30° C.) are added. 1.8375 g of the 2,2',6,6'-tetrafluoro-4,4'-dihydroxyazobenzene mixture are added by adding the appropriate amount of liquid dissolved from the previous step, taking into account the quantity of ethyl acetate added and any subsequent evaporation. The addition is carried out in a dropwise manner with manual stirring, to ensure no concentrated areas of the 2,2',6,6'-tetrafluoro-4,4'-dihydroxyazobenze are formed. The addition is carried out away from blue or UV light sources. A temporary opaque plastic cover with 5-10 small holes is placed on the container. This mixture is then placed in an adjustable vacuum oven, and 300 mm Hg of vacuum is applied for 30 minutes to de-gas the mixture.

Curing of the Mixture: A machined 4-piece type 316 stainless steel mold consisting of an end block with dimensions 50 mm×50 mm×3 mm and two set of threaded bolt holes, an outer block 705 mm×50 mm×50 mm, with a centered conical cavity extending the length of the mold, having a bore radius of 20 mm at one edge (where the end block is attachable), and a linear taper of the radius to 21.5 mm at a distance of 700 mm from the aforementioned edge, after which a constant radius of 21.5 mm extends for another 5 mm, with threaded bolt holes for attachment to the aforementioned end piece, a cylindrical inner block having a length of 705 mm and a constant radius of 18.5 mm, which may be secured to the end block at one edge by means of threaded bolt holes, and finally, a second end plate with dimensions 50 mm×3 mm×3 mm, into which are machined a shallow cavity 1 mm deep and 18.5 mm in radius, centered on the broad face of the piece, and having another depression 1 mm deep, on the same face, at all locations greater than 21.5 mm from the center, and further having a set of radial grooves approximately 0.1 mm wide and 0.1 mm deep extending from the center to the edge along at least four paths, is provided. The inner face of the end block, at the locations exposed to the cavity after assembly, is sprayed with Zyvax® 1070W mold release (used as-received from ChemTrend), as are the entirety of the curved surface of the inner block and the entirely of the curved surface of the outer block. The interior of the second end block (the face with the depressions) is also lightly sprayed with the mold release. The mold is then assembled by means of two sets of bolts that pass through the threaded holes on the end piece and into the matching threaded holes on the outer and inner pieces.

Immediately upon the completion of the de-gassing step, the previously mentioned mixture is carefully poured into the assembled mold, with the bolted end piece at the bottom and the long axis of the assembled mold aligned upright. A supporting assembly may be used to stabilize the mold in the upright position. The mold is filled to within 5 mm of the top of the cavity. The second end piece is then placed on top by means of matching the depressions in the piece with the ends of the outer and inner pieces. The filled mold and optional stabilizing assembly is then placed in the chamber of a temperature-controlled oven (Grainger item #53CM38, with shelves removed, two needles inserted through the door seal, one of which is connected to a metered nitrogen supply, and with a thermocouple inserted through the door seal for temperature control, and purged with a flow of 1 L/min of nitrogen gas. The oven temperature is then increased at 0.5° C. per minute until a temperature of 90° C. is obtained. This temperature is maintained for 1 hour, following which the temperature is increased at 0.5° C. per minute to 105° C. The temperature is maintained at 105° C. for 1 hour, then the oven is cooled by purging with a flow of 10 L/min of nitrogen gas with no heat supplied. The mold and optional support apparatus is removed from the oven. The unbolted end piece is then removed, and the solidification of the molded article is confirmed by tapping with a disposable wooden rod.

To de-mold the object, the bolts are loosened gradually, and, if necessary, the end piece is gently pried open. A metal rod having a diameter of 42 mm is then aligned with the center of the inner mold piece. By means of gently pushing this rod into the mold assembly, with stopping pins attached to the far end of the outer mold piece, detachment of the part from the outer piece is provided. Following this, a smaller metal rod having a diameter of 36 mm is aligned with the center of the inner mold piece at the same end, while a metal stopping collar having an inner diameter of 38 mm and aligned with the center of the inner mold piece, is placed at the far end of the part. By means of gently pushing the rod into the assembly, the detachment of the part from the inner mold piece is provided. One skilled in the art of de-molding glassy objects adjusts the release process as needed to secure the release of the part from the mold assembly without damage.

The surfaces of this as-molded item may be smoothed and finished to achieve a snug fit on a cylinder with an outer diameter of 37 mm. The object so formed is useful as a tool surface as part of a mandrel assembly, for example, for the molding of fiber-reinforced composite items of conical shape having a slight surface taper and precise dimensions. For use, the filament winding apparatus described by Mutasher et al. (Journal of Engineering Science and Technology, 2012, Vol. 7, pp. 156-168) is constructed, and the polyvinyl chloride mandrel described therein is replaced with a mandrel of identical dimensions made from type 316 stainless steel. Visual inspection of the images provided in the publication of Mutasher et al., along with the text, confirm the dimensions of the mandrel to be 700 mm long×25 mm in diameter. The mandrel is detached from the filament winder. To facilitate the release of parts, the mandrel is coated with a uniform 6 mm thick layer of Solcore 100 water-soluble tooling (as-received from Soltec, applied and cured per the manufacturer's instructions), and sprayed with Zyvax® 1070W mold release. The fabricated part is then slid over the mandrel. The mandrel and fabricated part are then immersed in a sand bath, then the sand bath with the mandrel and part are placed in the oven and heated at 0.5° C./min. to 260° C., while a 1 L/min. flow of nitrogen is provided inside the oven and the temperature is monitored as described previously. The temperature is then held constant for four hours, while nitrogen continues flowing at 1 L/min. After this, the nitrogen flow rate is increased to 10 L/min, the heat source is turned off, and the assembly is allowed to cool to ambient temperature, after which the mandrel and cured article are removed from the sand bath.

The nature of the Solcore 100, along with its very low coefficient of thermal expansion, make the surface undesirable for tooling cyanate ester composite parts with precisely tapered surfaces. The placement of the part with its tapered surface and more closely matched coefficient of thermal expansion provides an improved tooling surface.

Primaset® LECy cyanate ester formulations according to the state of the art will cure to principally cyanurate groups at a conversion of 65-70% when subjected to the initial process of heating to 105° C. in the mold, according to the published work of Hubbard et al. (ACS Appl. Mater. Interfaces, 2013, Vol. 5, pp. 11329-11335). Because the system described in this example employs virtually identical concentrations of reactive cyanate ester groups, phenol groups, and copper ligands, the same cure kinetics are realized and the system cures to near 70% conversion. Further, according to this work, and applying the DiBenedetto equation for Primaset® LECy described in Reams et al. (ACS Appl. Mater. Interfaces, 2012, Vol. 4, pp. 527-535) while substituting the glass transition temperature at full cure measured by Hubbard et al. of 260° C. into the equation parameters to account for the differences in reactive phenol concentration, the glass transition temperature at 70% conversion for the network described in this example is expected to be near 105° C. Because further conversion of the unreacted cyanate ester groups would result in a glass transition higher than the cure temperature, the rate of conversion slows to near zero once a conversion near 70% is achieved. As described by Hubbard et al., at conversions near 70%, polycyanurate networks are solid substances that can be handled without damage if handled with care. By means of the same logic, one may deduce that the second cure step to 260° C. will result in a conversion near 100%, as confirmed by the analysis provided in Hubbard et al.

According to the data provided by Reams et al., and confirmed by Guenthner et al. (Macromolecules, 2014, Vol. 47., pp. 7691-7700), the densities of state of the art networks derived from Primaset® LECy decrease as conversion increases from 70% to near 100%, however, the extent of the decrease is not dependent on the cure path taken. Achieving carefully controlled changes in density during cure is important in this example. The decrease in density will result in an expansion of the part. During the initial cure, such an expansion can make successful de-molding of the part without damage more difficult. During the secondary cure, such expansion may compromise the fit with the mandrel, lead to disbonding with the mandrel, or lead to built-in stresses causing undesirable dimensional changes in the part. A desirable characteristic of the invention is that the formulation of the system combining photo-isomerizable groups (azobenzene) and reactive groups (phenol and cyanate ester) provides a separate means of controlling dimensional changes. According to the work of Agolini and Gay (Macromolecules, 1970, Vol. 3, pp. 349-351), the density of polymers containing azobenzene groups, such as those formed during the cure of the cyanate ester/azobenzene formulation in this example, differ substantially. Moreover, according to Bléger et al., thermal treatment of the azobenzene groups results in a predictable interconversion between cis- and trans-states, with time constants at temperatures of 90-105° C. on the order of 1 hour, and with time constants decreasing substantially as the temperature is increased. Inclusion of the photo-isomerizable group in the formulation therefore provides a significant advantage, in that a new means of precisely controlling the dimensional changes of the part on cure is provided. For instance, by providing a longer or shorter cure times at 105° C., one alters the ratio of cis- to trans-structures, thereby changing the volume of the part without substantially changing the conversion. By further altering the initial concentration of photo-isomerizable group, one may control both the change in volume on initial cure and the change in volume on secondary cure.

Example 4—Iterative Process of Examples 1-3

The stainless steel mandrel with the cured tool as described in Example 1 is then reattached to the filament winding device and sprayed liberally with a mold release. The curative mixture is placed within the resin bath on the filament winder. If needed, an immersion heater is also placed in the resin bath to maintain the temperature needed to maintain adequate liquidity of the mixture. A spool of carbon fiber (Hextow AS4, 12K filament grade) is then loaded into the winder, passed through the resin bath, and wound at a 55 angle as described by Mutasher et al. Initially, the filament is built up in a scrap area. The spreading elements are adjusted to maintain a tow width of 6 mm. When stable and on-target conditions are achieved, the winder begins traversing the mandrel. A total of 39 traverses each way is completed to lay down a total of 6 layers (at crossed orientations) of the fibers. The mandrel and wound item are then removed from the device, with the cured resin tool still in place. The wound item is then placed, still on the mandrel and tool, in the oven, with a protective bag emplaced to minimize drippage, and with a nitrogen purge and temperature monitoring in place as described in Example 1. The initial cure takes place by heating at 2° C./min. to 105° C., followed by one hour at 105° C. In a second cure step, the temperature is raised to 200° C. by heating at 0.5° C./min, and held at 200° C. for four hours. The oven is then allowed to cool as in Example 1. When ambient temperature is reached, the SolCore tool is dissolved by pressure washing with cold water, enabling release of the mandrel. As in Example 1, a metal rod with a diameter of 39 mm is placed at the thinner end of the composite structure, while the far end is held in place. The rod is then pushed gently to release the part from the tool. The composite item, in the form of a slightly tapered cone, is then polished as needed and fitted with end attachments as desired. Such a composite item, due to its precisely controlled shape, heat resistance, and good dielectric transmission properties, is useful as a forward radome on the nose projection of a six-passenger private jet aircraft.

In this example, as in Example 1, the additional predictable shrinkage and expansion characteristics afforded by formulation of the photo-isomerizable ingredient with the reactive groups and the thermally stable groups, provides the advantage of enabling one skilled in the art of composite part design to adjust the dimensional changes produced by the cure process independently of adjusting other characteristics, such as the final conversion of the part, de-molding conditions, and cure conditions.

Example 5—Preparation of Epoxy Reagent

In a 500-mL Erlenmeyer flask is placed 2.0 g of the 2,2',6,6'-tetrafluoro-4,4'-dihydroxyazobenzene, prepared as in Example 1, a large stoichiometric excess of epichlorohydrin (99%, purchased from Sigma-Aldrich) (12.9 g), and 250 mL of ethanol (ACS Reagent Grade, purchased from Sigma-Aldrich). The mixture is heated to 90° C., following which 5 mL of a 20% aqueous solution of NaOH (NaOH purchased from Sigma-Aldrich) is added drop-wise. The mixture is allowed to stir while maintaining the temperature at 90° C., followed by cooling to room temperature. The mixture is then divided into three equal portions, each of which is mixed with 200-mL methylene chloride (ACS Reagent Grade, from Sigma-Aldrich) in a 500-mL Erlenmeyer flask and shaken vigorously. Following this, each of the mixtures is allowed to separate into two layers, with the aqueous layer removed from each by carefully decanting. Following this, 200 mL of deionized water is added to each flask, the mixture vigorously shaken, and again allowed to separate with careful decanting of the aqueous layer. This washing step is repeated two more times for each mixture. Following this each organic layer is then dried using 5 g magnesium sulfate, which is removed by filtration. Finally, Each of the organic layers is then placed in a rotary evaporator (as previously described) and the solvent removed, yielding a total of 2.3 g of product (diepoxide of 2,2',6,6'-tetrafluoro-4,4'dihydroxyazobenzene, henceforth abbreviated as "fluoro-azo-epoxy")

Example 6—Photoconversion of Epoxy Reagent

A Unigsys FlowSyn reaction system is assembled with the following components: PhotoSyn reactor with 260 1-W 455 nm LEDs (along with blue/green/white variable wavelength LED replacement), UQ1053 Polar Bear Plus temperature control unit, UQ1063 pump with pressure transducer, UQ1100 flow UV spectrophotometer, UQ1102 flow cell and optical fibers for spectrophotometer, FlowControl software, and UQ9500 logging kit for PC. The flow path is designed so that fluid passes from a feed bottle, through the pump, then the temperature control unit, then the reactor, and then the spectrophotometer before being collected in a receiving bottle. The software is installed on a Dell Inspiron 17 7000 series laptop connected to the unit. In a clean large glass bottle (200-mL marked capacity from the Uniqsis UQ6000 bottle kit), 200-mL of ethyl acetate (ACS Reagent, ≥99.5%, from Sigma-Aldrich) is added. The bottle, along with a second clean, empty receiving bottle, is connected to the reaction system. The pump, temperature control unit, and spectrophotometer are started, and the system is purged with ethyl acetate at a flow rate of 20 mL/min. for 10 minutes at a temperature of 20° C., while a baseline UV-Vis spectrum is collected.

In a clean large glass bottle (200-mL marked capacity from the Uniqsis UQ6000 bottle kit, with closure removed) is placed 2.0 g of the fluoro-azo-epoxy, prepared as described previously, to which is added 200 mL of ethyl acetate (ACS Reagent, ≥99.5%, from Sigma-Aldrich) and a Teflon-coated disposable magnetic stir bar (Fischer Scientific #14-513-95). A temporary cap is placed on the bottle and the bottle is placed on a stir plate (Corning™, Product #6796420D). The mixture is stirred at room temperature for 10 minutes, or until complete dissolution is noted. The temporary cap and stir bar are removed, and the matching special closure from the UQ6000 kit is placed on the bottle. The bottle is then connected to the assembled Uniqsis reaction system in place of the ethyl acetate feed. The receiving bottle is replaced with an empty bottle and re-connected to the system. The cooling unit is engaged and the pressure adjusted to maintain a flow rate of 20 mL/min. The optical output power is adjusted to 15 W. These conditions are maintained for approximately 10 minutes (or until all but 5 mL of the feed fluid is consumed if the flow rates are adjusted during the procedure) while the spectrophotometer records the spectrum of material passing through. Per the description and data for a number of substantially similar chemical compounds provided by Bléger et al., p. 20598-20599, one skilled in the art of interpreting ultraviolet-visible light spectra determines the ratio of azobenzene isomers produced on a continuous basis, and by means of adjusting pressures and optical power intensities, ensures that photo-conversion of 70 mol % of the trans (E) isomer to cis (Z) isomer takes place. In the event that the blue light source provides inadequate conversion, the variable wavelength LED is optionally substituted and the wavelength adjusted to provide more selective irradiation of the trans isomer. In the event that more than 70% photo-conversion cannot be avoided, a portion of the starting solution is withheld from the process and added to the receiving bottle once the process is complete, so as to dilute the quantity of photo-converted material appropriately. One skilled in the art of solution blending determines the appropriate quantity to withhold by means of an algebraic formula involving the observed photo-conversion of material passed through the reaction system.

The photo-converted material is concentrated by applying vacuum after transferring the solution to a reduced pressure rotary evaporator (Büchi® Rotavapor R-100) shielded from ambient light, until the amount of solvent recovered reaches about 200 mL. The concentrated material may form co-crystals or remain as a viscous oil, however the presence of a 70:30 mixture provides a eutectic effect that lowers the melting point of any co-crystals. If needed, the melting point of the mixture after concentration is determined by one skilled in the art of measurement with an Omega MPS10-240 melting point apparatus.

Example 7—Preparation of a Curative Mixture and Curing of the Mixture

In a 40-mL glass scintillation vial (wrapped in aluminum foil to shield it from light) with Teflon-lined cap is placed 1.5 g of the aforementioned fluoro-azo-epoxy mixture prepared as previously described in Example 5, along with a stoichiometric amount, based on total active hydrogen count (0.373 g) of 4,4'-methylenedianiline (97%, Sigma-Aldrich). If the melting temperature of the mixture is below 50° C., the mixture is heated to 10° C. above the melting temperature. Otherwise, 0.5 g portions of ethyl acetate (ACS Reagent, ≥99.5%, from Sigma-Aldrich) are added with the vial sealed tightly until the mixture is liquid at 60° C. A disposable Teflon-coated stir bar (Fischer Scientific #14-513-9) is added. The bottle is placed on a stir plate (Corning™, Product #6796420D) while the temperature is maintained at 60° C., while the contents are stirred. This mixture is then placed in an adjustable vacuum oven, and 300 mm Hg of vacuum is applied for 30 minutes to de-gas the mixture. This de-gassing step is repeated as necessary to reduce the amount of ethyl acetate present to less than 5% of the total of epoxy and dianiline present.

Curing of the Mixture: Immediately after mixing an de-gassing, a machined 1-piece type 316 stainless steel mold, consisting of a 5 cm×5 cm×6.35 mm block into which is machined a circular depression 2 cm in diameter and 2 mm deep on the center of one of the broad faces, is sprayed with Zyvax® 1070W mold release (used as received from ChemTrend. A small portion of the prepared epoxy/dianiline mixture is then carefully poured into the mold in a thin stream, ensuring that no air bubbles are entrained in the mold, until the cavity is filled but not overflowing.

The filled mold is then placed in the chamber of a temperature-controlled oven (Grainger item #53CM38, with shelves removed, two needles inserted through the door seal, one of which is connected to a metered nitrogen supply, and with a thermocouple inserted through the door seal for temperature control, and purged with a flow of 1 L/min of nitrogen gas. The oven temperature is then increased at 0.5° C. per minute until a temperature of 90° C. is obtained. This temperature is maintained for 1 hour, following which the temperature is increased at 0.5° C. per minute to 125° C. The temperature is maintained at 125° C. for 4 hours, then the oven is cooled by purging with a flow of 10 L/min of nitrogen gas with no heat supplied. The mold is removed from the oven, and the object (a cured disc) de-molded by tapping on the reverse side or edges of the mold as needed.

The cured disc of material is useful as a covering for a sensor port of an aircraft. As such, its density must be carefully controlled to propagate electromagnetic signals in a manner that is precisely defined for the purpose of interpreting these signals correctly. Epoxy resins are known to shrink slightly during cure, making precise control of density difficult. However, as indicated in Example 8 below, the transformation from cis- to trans-groups will produce a lowering of the density of the cured material, counteracting the shrinkage induced by cure, and thereby providing a useful means of controlling dimensional changes. Moreover, shrinkage of the part may be counteracted by further transformation of cis- to trans-groups using a free-standing post-cure, in which monitoring of dimensional changes as a function of time and temperature enables one skilled in the art to produce through iterative methods a part with the precisely tuned dimensions.

Example 8—Measurement of the Changes in Volume for Example 6 Via Physics-Based Model To asses changes in volume, the Schrödinger Material Science Suite Release 2020-1 was utilized. This system has been shown to reliably capture the trend changes in density due to alterations of chemical structure, such as cis- to trans-conformational difference, as well as changes in density due to cure, for numerous thermosetting resin systems, including epoxy resins (Krauter et al., "COMPOSITE MATRIX DESIGN WITH EFFICIENT COMPUTATIONAL CHEMISTRY APPROACHES", ECCM18—18th European Conference on Composite Materials Athens, Greece, 24-28 Jun. 2018) and cyanate ester resins (Moore et al., "Molecular Modeling of Polycyanurates to Predict Thermophysical Properties", American Chemical Society Fall 2019 National Meeting and Expo, San Diego, California, 25-29 Aug. 2019).

The following two systems were created using the Disordered System Build workflow with default settings (including the OPLS3e force field): System #7-1: cis-fluoro-azo-epoxy, 238 molecules, trans-fluoro-azo-epoxy, 102 molecules, 4,4'-methylenedianiline, 170 molecules. System #7-2, cis-fluoro-azo-epoxy, 102 molecules, trans-fluoro-azo-epoxy, 238 molecules, 4,4'-methylenedianiline, 170 molecules. The resulting systems of 510 molecules are similar in size to published systems that provide good predictive power. The resultant disordered systems were then subjected to a Multi-Step Molecular Dynamics workflow, including a Materials Relaxator preparative step, 10 ns of molecular dynamics at 300 K using a 2 fs time step, and analysis of density. For each system, the Multi-Step Molecular Dynamics workflow was repeated at a temperature of 550 K using the output from the 300 K step. For each system, the output from the 550 K step was then subjected to a Cross-Linking workflow, using an 800 K temperature, a 3 to 5 Angstrom search radius, 50 ps of relaxation time, a maximum of 10 cross-links formed per iteration, and a halt at either 98% of epoxy groups cross-linked or 20 unproductive cross-link iterations. For each system, the cross-linked systems were then subject to 5 ns of molecular dynamics starting at 800 K, then 795 K and decreasing by 15 K until 105 K using the Thermophysical Properties workflow. At the end of each step, the density of each system was measured.

For System #7-1 (70% cis) the density at 300 K prior to cure was 1.294 g/cc, while after cross-linking, the density was 1.311 g/cc, a shrinkage of 1.3%. For system #7-2 (30% cis), the density was 1.297 g/cc, whereas after cross-linking, the density was 1.304 g/cc, a shrinkage of 0.8% using the 70% cis-system as a baseline. These data illustrate that the conversion of cis- to trans-provides a useful mechanism to adjust shrinkage during the cure process, as well as the adjust the density of the final part. Because both parameters are important (shrinkage during cure leads to undesirable residual stresses that also impact final part geometry over time), the use of the proper cis- to trans-ratio as selected by those skilled in the art enables simultaneous satisfaction of density and shrinkage requirements.

Example 9—Preparation and Cure of Mixture Derived from Trans-Resveratrol

Trans-resveratrol epoxy may be prepared as described in the published work of Garrison et al. (*ACS Sustainable Chem. Eng.* 2020, 8, 37, 14137-14149), and subjected to the same photoconversion, preparation, and cure processes described in Examples 6 and 7 (albeit with the added weights of 4,4'-methylenedianiline and epichlorohydrin to maintain the same stoichiometric ratios provided in these examples, and with a final cure temperature of up to 280° C., which has been shown by Cambrea et al. (*J. Polym. Sci., Part A: Polym. Chem.* 2017, 55, 971-980) to produce complete cis- to trans-conversions in cyanate esters based on resveratrol). Alternatively, the photoconversion step may be performed on the phenolic precursor, and the mixture of photo-isomers subjected to epoxidation, as the times and temperatures involved in epoxidation are not sufficient to induce large changes in cis- to trans-ratios given the activation energy described by Cambrea et al.

As with Example 8, in order to illustrate the effect of cis- to trans-isomerization on the density and shrinkage of these monomers, two systems, #10-1, comprised of 292 cis-resveratrol epoxy molecules and 219 molecules of 4,4-methylenedianiline, and system #10-2, comprised of 292 trans-resveratrol epoxy molecules of 219 molecules of 4,4-methylenedianiline, were prepared using the Schrödinger Materials Science Suite. Using procedures identical to those described in Example 8, the pre-cross-linking densities were 1.165 g/cc for system #10-1 and 1.165 g/cc (very similar to #10-1) for system #10-2. The post cross-linking densities were 1.181 g/cc for system #10-1 and 1.170 g/cc for system #10-2. As with example 8, but this time in more extreme form given the greater difference in cis- to trans-ratio, the shrinkage can be adjusted between 1.4% and 0.4% through use of the cis- to trans-conversion.

Example 10—Chemical Analysis of an Epoxy Reagent

An epoxy reagent sample prepared from resveratrol, according to the description in Example 9, was analyzed by gel permeation chromatography as follows. A small portion of the epoxy resin as prepared in a mixed state of cis and trans isomers, was dissolved in tetrahydrofuran at a concentration of 5 mg/mL. 25 microliters of the solution was then injected into the column set of an Agilent 1090 HPLC. The column set used was a series of (Phenogel 5-micron, 300× 4.6 (inner diameter) mm, 1 500 Angstrom+2×100 Angstrom, without guard. Following injection the refractive index of the effluent was recorded using a Waters 2414 Refractive Index detector at a sensitivity setting of 64x. The flow rate was 0.35 mL/min, with oven and detector temperature settings at 40° C. Retention times were converted to relative molecular weights using a calibration curve plotted using a second order polynomial fit of retention time (min.) vs. log molecular weight prepared from the injection of narrow molecular weight polystyrene standards with molecular weights of 19720, 9920, 4490, 2360, 1180, 598, 494, 390, 286 and 182 g/mol. Toluene was added as a low molecular weight marker.

Figure 3:
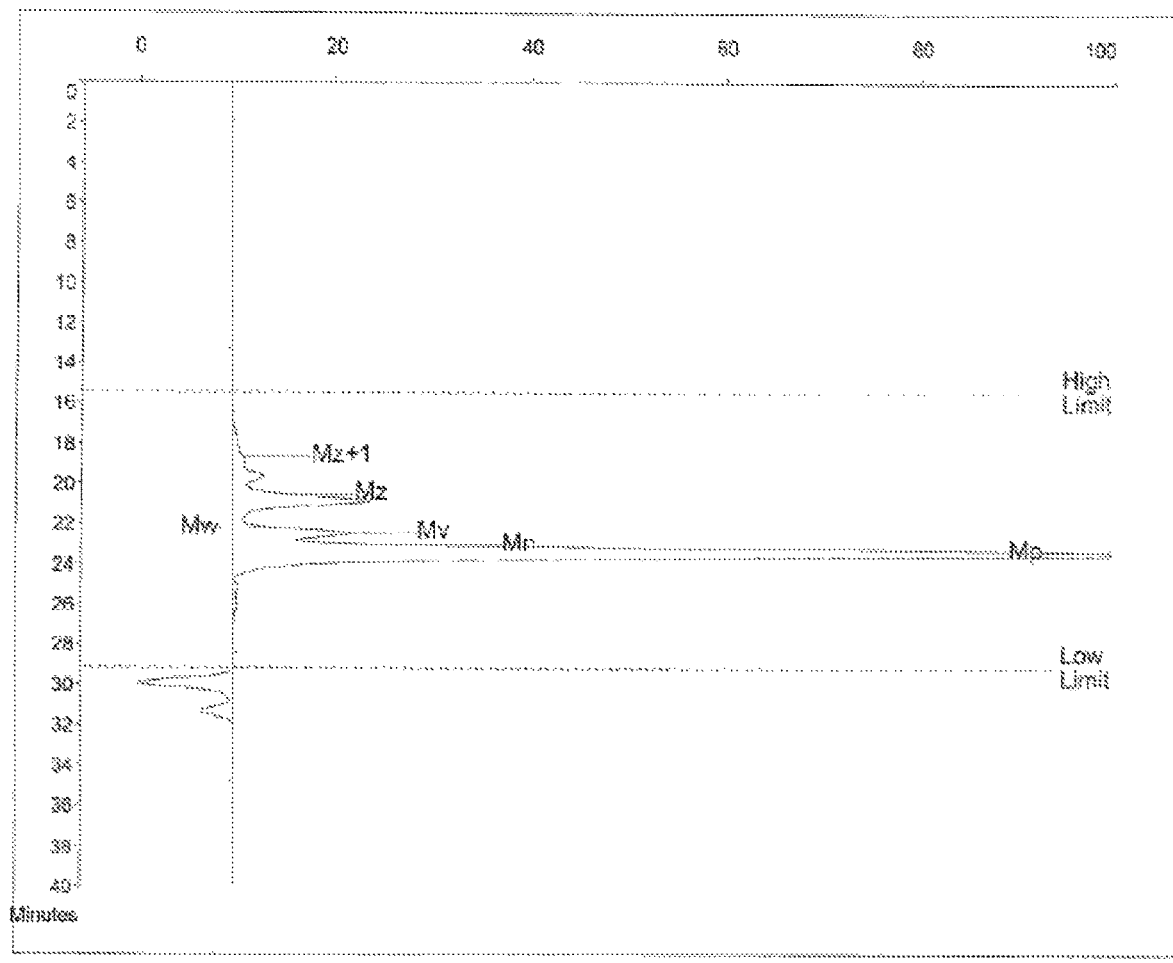
FIG. 3 is a chromatogram of a sample of a monomeric composition of matter consistent with the embodiments disclosed herein.

According to FIG. 3, the resultant chromatogram exhibited a distinctive and unusual pattern for a mainly monomeric epoxy resin species. Typically, the resultant chromatograms exhibit a series of peaks whose spacing becomes more separated in time in a monotonic fashion as retention time increases, with a smooth and monotonic increase in peak height with retention time. When converted to molecular weight, these peaks crudely correspond to near-multiples of the molecular weight of the monomeric species (1, 2, 3, etc.) with a relatively constant correction factor close to one, corresponding to the difference in the molecular weight vs. radius of gyration characteristics between the polystyrene standards and the sample material. These peaks represent an oligomeric series (monomer, dimer, trimer, etc.), which are well-known to arise in the synthesis of epoxy resins due to coupling of partially converted reactants. The pattern in FIG. 3, however, is a "doublet of doublets", a set of two peaks only slightly displaced in time, more widely separated from another set of two peaks. In FIG. 3 the ratio of peak areas in the closely-spaced peaks is between 13:100 and 25:100. The larger spacing between corresponding peaks in the two "doublets" was translated to a molecular weight of 314 g/mol and 813 g/mol, which represents monomeric and dimeric species with a correction factor of 0.8 and 1.1, respectively. These values are highly consistent with expected values of such correction parameters. They would also imply a dimer to monomer ratio of 20%, which is within the expected range. On the other hand, if the four peaks represented monomer, dimer, trimer, and tetramer, then the ratio of dimer to monomer would be only 10-15% but the ratio of trimer to dimer would be considerably greater than 100%, with the ratio of tetramer to trimer again falling to 25%. It is implausible that side reactions would form a small amount of dimer but then favor the formation of trimer and not tetramer Thus, the pattern is consistent with an oligomeric series comprising 10 mol % to 25 mol % of an alternate monomeric form having a very similar or identical molecular weight, with monomer and a small quantity of dimer visible in the chromatogram. Given that product purity of materials prepared in Example 9 does not indicate a large quantity of residual side products, the best explanation for this unusual pattern is the presence of cis and trans isomers. Moreover, the product of this reaction is a slowly crystallizing semi-solid material, consistent with the beneficial retarding effect of cis isomer on the crystallization of otherwise pure trans material.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a plurality of molecules, the plurality of molecules collectively comprising:
   a. at least one photo-isomerizable radical;
   b. at least one thermally reactive radical; and
   c. at least one thermally stable radical,
   wherein one or more photo-isomerizable radicals of the at least one photo-isomerizable radical optionally comprises one or more thermally stable radicals of the at least one thermally stable radical,
   wherein all or a fraction of the molecules of the plurality of molecules independently have a structure of Formula V:

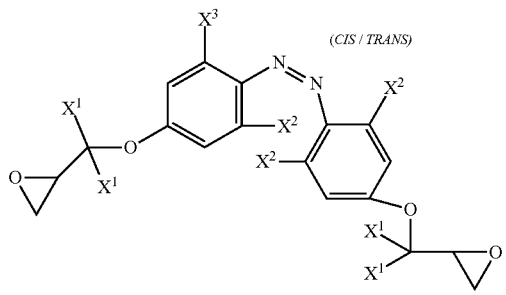

Formula V wherein:
   each $X^1$ is independently $CH_3$ or H;
   each $X^2$ is independently selected from the group consisting of: H, F, a halomethyl, and $CH_3$; and
   the compound of Formula V has a cis or trans configuration, and
   wherein each $X^1$ is H and each $X^2$ is F.

* * * * *